US006403098B1

(12) United States Patent
Burke et al.

(10) Patent No.: US 6,403,098 B1
(45) Date of Patent: Jun. 11, 2002

(54) ROTAVIRUS VACCINE FORMULATIONS

(75) Inventors: Carl J. Burke, Pennsburg; David B. Volkin, Doylestown, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/366,616

(22) Filed: Aug. 3, 1999

Related U.S. Application Data

(63) Continuation-in-part of application No. 08/938,260, filed on Sep. 26, 1997, now Pat. No. 5,932,223.

(60) Provisional application No. 60/026,754, filed on Sep. 26, 1996, and provisional application No. 60/046,760, filed on May 16, 1997.

(51) Int. Cl.[7] .............................................. A61K 39/15

(52) U.S. Cl. ................. 424/215.1; 424/93.6; 424/93.1; 435/235.1

(58) Field of Search ............................ 424/215.1, 93.1, 424/93.6; 435/235.1

(56) References Cited

U.S. PATENT DOCUMENTS

| | | | |
|---|---|---|---|
| 5,626,851 A | * | 5/1997 | Clark et al. |
| 5,750,109 A | | 5/1998 | Clark et al. |
| 5,827,534 A | | 10/1998 | Fasano |

FOREIGN PATENT DOCUMENTS

| | | |
|---|---|---|
| EP | 0 065 905 A1 | 5/1982 |
| EP | 0 192 404 A2 | 2/1986 |
| WO | WO 96/01651 | 1/1996 |

OTHER PUBLICATIONS

Gajardo, et al., "Two Proline Residues Are Essential in the Calcium–Binding Activity of Rotavirus VP7 Outer Capsid Protein", Journal of Virology, vol. 71, No. 3, Mar. 1997, pp. 2211–2216.

Ludert, et al., "Penetration and Uncoating of Rotaviruses in Cultered Cells", Intervirology, vol. 27, pp. 95–101, 1987.

Shirley, et al., "The Influence of Divalent Cations on the Stability of Human Rotarvirus", Archives of Virology, vol. 67, pp. 1–9, 1981.

Meng, et al., "Physicochemical Stability and Inactivation of Human and Simian Rotaviruses", Applied and Environmental Microbiology, vol. 53, No. 4, pp. 727–730, 1987.

Willoughby, et al., "SA11 Rotavirus Is Specifically Inhibited by an Acetylated Sialic Acid", The Journal of Infectious Diseases, vol. 161, pp. 116–119, 1990.

Fukudome, et al., "Comparison of Human, Simian and Bovine Rotaviruses for Requirement of Sialic Acid in Hemagglutination and cell Adsorption", Virology, vol. 172, 99. 196–205, 1989.

Superti, et al., "Effect of Polyions on the Infectivity of SA–11 Rotavirus in LCC–MK2 Cells", Comp. Immun. Microbiol. Infect. Dis., vol. 16, No. 1, pp. 55–62, 1993.

Garbag–Chenon, et al., "Reactogenicity and Immunogenicity of Rotavirus WC3 Vacine in 5–12–Month Old Infants", Res. Virol., vol. 140, pp. 207–217, 1989.

Mendez, et al., "Binding to Sialic Acids Is Not an Essential Step for the Entry of Animal Rotaviruses to Epithelial Cells in Culture", J. of Virology, vol. 67, No. 9, Sep. 1993, pp. 5253–5259.

Ducan, et al., "Comparative Analysis of Oral Delivery Systems For Live Rotavirus Vaccines", J. of Controlled Release, vol. 41, pp. 237–247, 1996.

Ruiz, et al., "The Concentration of Ca2+ That Solybilizes Outer Capsid Proteins from Rotavirus Particles Is Dependent on the Strain", Journal of Virology, vol. 70, No. 8, pp. 4877–4883, 1996.

Yolken, et al., "Intestinal Mucins Inhibit Rotavirus Replication in an Oligosaccharide–Dependent Manner", The Journal of Infectious Disease, vol. 169, pp. 1002–1006, 1994.

Shahrabadi, et al., "Further Analysis of theRole of Calcium in Rotavirus Morphogenesis", Virology, vol. 158, pp. 103–111, 1987.

Ward, et al., "Comparative Study on the Mechanisms of Rotavirus Inactivation oby Sodium Dodecyl Sulfate and Ethylenediaminetetraacetate", Applied and Environmental Microbiology, vol. 39, No. 6, pp. 1148–1153, 1980.

Estes, et al., "Rotavirus Stability and Inactivation", J. Gen. Virol., vol. 43, pp. 403–409, 1979.

Dormitzer, et al., "Calcium Chelation induces a Conformational Change in Recombinant HerpesSimplex Virus–1–Expressed Rotavirus VP7", Virology, vol. 189, pp. 828–832, 1992.

Chen, et al., "Determinants of Rotavirus Stability and Density During CsCl Purification", Virology, vol. 186, pp. 228–237, 1992.

Christy, et al., "Evaluation of a Bovine–Human Rotavirus Reassortant Vaccine in Infants", Journal of Infectious Disease, vol. 168, pp. 1598–1599, 1993.

Kabayashi, et al., "Tetravalent Rhesus Rotavirus Vaccine in Young Infants", Journal of Infectious Disease, vol. 170, pp. 1260–1263, 1994.

Ing, et al., "Immunogenicity of Tetravalent Rhesus Rotavirus Vaccine Adminsitered With Buffer and Oral Polio Vaccine", AJDC, vol. 145, pp. 892–897, 1991.

(List continued on next page.)

*Primary Examiner*—Donna Wortman
(74) *Attorney, Agent, or Firm*—Michael D. Yablonsku; Jack L. Tribble

(57) ABSTRACT

The present invention provides novel liquid and lyophilized formulations of vaccines against rotavirus infection and methods of their preparation. The formulations include buffering agents appropriate for oral administration of rotavirus vaccines. The formulations also include compounds to stabilize of the vaccine compositions against loss of potency.

13 Claims, 14 Drawing Sheets

OTHER PUBLICATIONS

Vesikari, et al., "Increased 'Take' Rate of Oral Rotavirus Vaccine in Infants After Milk Feeding", The Lancet, pp. 700, 1984.

Borian, et al., "The Effect of Buffer on the Immune Response of Oral Rotavirus Vaccine", Ped. Res., vol. 23, No. 982, pp. 365A, 1988.

Flores, et al., "Reactogenicity and Immunogenicity of a High–Titer Rhesus Rotavirus–Based Quadrivalent Rotavirus Vaccine", Journal of Clinical Microbiology, Sep. 1993, vol. 31, No. 9, pp. 2439–2445.

Rennels, et al., "Safety and Efficacy of High–Dose Rhesus–Human Reassortant Rotavirus Vaccines—Report of the National Multicenter Trial", Pediatrics, No1. 97, No. 1, Jan. 1996, pp. 7–13.

Linhares, et al., Immunogenicity, safety, and efficacy of tetravalent rhesus–human, reassortant rotacirus vaccine in Belem, Brazil, Bull. World Health Organization, vol. 75, No. 5, pp. 491–500, 1996.

Gilligan, et al., "Oral Vaccines: Design and Delivery", J. of Pharmaceuticals, vol. 75, pp. 1–24, 1991.

Graham, et al., "Minimal Infective Dose of Rotavirus", Arch. Virol., vol. 92, pp. 261–271, 1987.

Pichichero et al., "A comparative evaluation of the safety and immunogenicity of a single dose of unbuffered oral rhesus serotype 3 . . . ", Vaccine, vol. 11, Issue 7, pp. 747–753, 1993.

Georges–Courbot, et al., "Evaluation of the efficacy of a low–passage bovine rotavirus (strain WC3) vaccine in children in Central Africa", Res. Virol., vol. 142, pp. 405–411, 1991.

Vesikari, et al., Clinical trials of live oral rotavirus vaccines: the Finnish experience, Vaccine, vol. 11, Issue 2, 1993, pp. 255–261.

Weiss, et al., Rapid Inactivation of Rotaviruses by Exposure to Acid Buffer or Acidic Gastric Juice, J. Gen. Virol., vol. 66, pp. 2725–2730, 1985.

* cited by examiner

ROTAVIRUS VACCINE FORMULATIONS

CROSS-REFERENCE TO RELATED APPLICATIONS

This application claims the benefits of U.S. Provisional Application Ser. No. 60/026,754, filed Sep. 26, 1996 and U.S. Provisional Application Ser. No. 60/046,760, filed May 16, 1997 and is a continuation-in-part of U.S. application Ser. No. 08/938,260, filed Sep. 26, 1997, now U.S. Pat. No. 5,932,223.

STATEMENT REGARDING FEDERALLY-SPONSORED R&D

Not applicable.

REFERENCE TO A MICROFICHE APPENDIX

Not applicable

1. Field of the Invention

The present invention is related to novel liquid and lyophilized formulations of rotaviruses useful as vaccines and methods for their preparation.

2. Background of the Invention

Rotaviruses (RV) cause acute gastroenteritis, a disease that requires hospitalization of infants and young children in developed countries, and a frequent cause of death in children less than 5 years of age in developing regions of the world. Studies in the United States, Australia, and Japan have demonstrated that between 34 and 63% of hospitalizations of children for acute diarrheal disease are associated with rotavirus infection. The incidence of hospitalization for rotavirus gastroenteritis in a health maintenance organization in the U.S. was estimated to be 222 per 100,000 in children from 13 to 24 months of age, and 362 per 100,000 in those less than one year. Infection with rotavirus was associated with 63% of all hospitalizations for acute diarrhea in this pediatric population. A review of mortality data in the U.S. from 1973 to 1983 indicated that 500 deaths per year occur in children less than 4 years old due to diarrheal diseases, and that 20 to 80% of excess winter deaths due to diarrhea in the U.S. are associated with rotavirus infections. Rotaviruses are also responsible for substantial proportion of the mortality associated with diarrheal diseases in third world countries. An effective rotavirus vaccine would therefore have a major impact on the health of children in both the developed and developing areas of the world.

Rotaviruses have an inner and outer capsid with a double-stranded RNA genome formed by eleven gene segments. Multiple serotypes have been defined by plaque reduction neutralization tests, and studies of reassortant viruses have demonstrated that two outer capsid proteins, VP7 and VP4, are the determinants of virus serotype. The VP7 protein is coded for by either gene segment 7, gene segment 8 or gene segment 9 of a particular human rotavirus. The location of the VP7 encoding gene may be determined for each specific rotavirus by conventional experimental methods. The VP4 protein is an 88,000 dalton major surface structural protein product of gene 4 of a rotavirus. Like VP7, it functions as a major serotype-specific antigen, operative in serum neutralization (SN) tests, capable of inducing serotype-specific neutralizing antibody, and capable in a mouse system of inducing serotype-specific immune protection against rotavirus disease. In some earlier references, the VP4 was referred to as VP3. After 1988, a change in nomenclature, resulted in the more proper reference to this protein as VP4.

Since the gene segments encoding the VP7 and VP4 proteins segregate independently, it has been proposed that serotyping nomenclature include both the G type, determined by VP7, and the P type, determined by VP4. Most human rotavirus infections in the U.S. are caused by viruses of G types 1, 2, 3, or 4, and P types 1, 2, or 3. However, other human rotavirus types, including for example, type G9, are more prevalent in Asia, Europe and certain third world countries.

A number of animal rotaviruses are attenuated in humans, and have been evaluated as potential live rotavirus vaccines, including the bovine serotype G6 WC3 rotavirus. The WC3 vaccine virus was shown to be immunogenic and non-reactogenic in infants, but was inconsistent in providing protective immunity against human rotavirus infection. It has been suggested that serotype-specific immunity is necessary to include consistent protection against rotavirus diarrhea.

There exists a need to the art for effective vaccines providing protective immunity against rotavirus infection and the severe clinical symptoms associated therewith.

For worldwide distribution of rotavirus vaccines, it is necessary to formulate vaccines such that they are stable under a variety of environmental conditions. Components used to stabilize vaccines are known. However, particular formulations of components useful to stabilize rotavirus vaccines must be determined experimentally. One object of the present invention is present formulations which stabilize rotavirus vaccines.

SUMMARY OF THE INVENTION

The present invention provides novel formulations of rotaviruses useful as vaccines and methods for their preparation.

DETAILED DESCRIPTION OF THE INVENTION

Figure 1A:
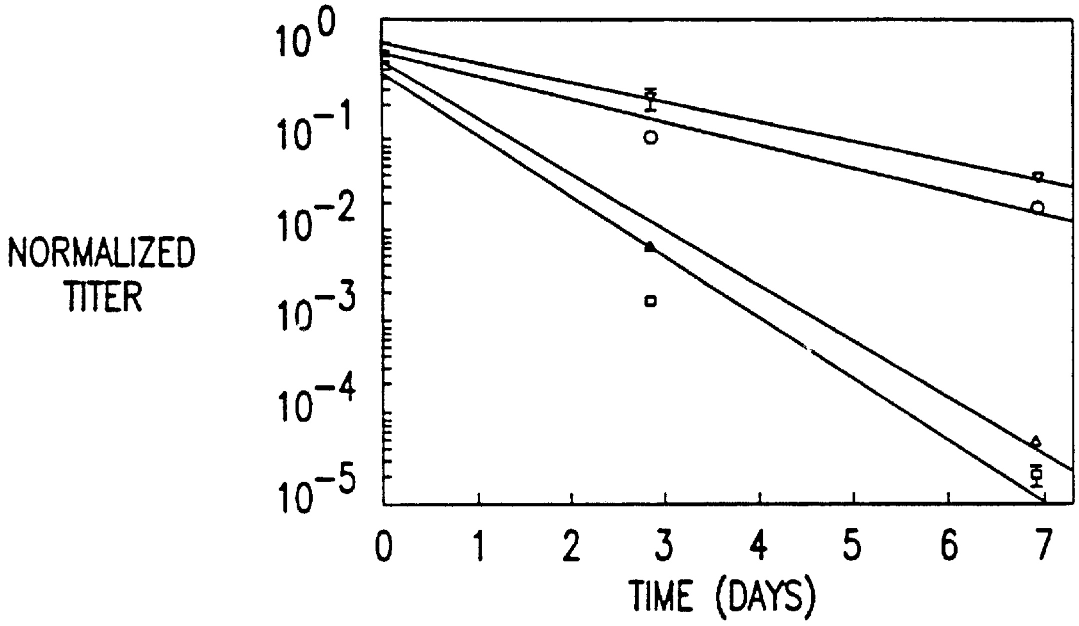
FIG. 1. Effect of buffer combinations on rotavirus stability at 37° C. for 1 week. Data for the G1 reassortant are shown in panel A and the P1 reassortant in panel B. All values are expressed as pfu/mL normalized to the reference, or 0 day, sample. The buffer combinations are represented as follows: 0.05 M sodium citrate+0.15 M sodium bicarbonate (□), 0.05 M sodium citrate+0.15 M sodium phosphate (○), 0.05 M lactic acid+0.15 M sodium bicarbonate (Δ), 0.05 M lactic acid+0.15 M sodium phosphate (▽) and 0.20 M sodium succinate+0.05 M sodium phosphate (◇). All formulations have pH values of 7.

The present invention provides novel formulations of rotaviruses useful as vaccines and methods for their preparation. More particularly, the invention relates to stabilizing formulations for liquid and lyophilized rotavirus vaccines. In addition, some of these formulations can be orally delivered either with or without preneutralization of gastric acid since some of the formulations contain high levels of buffering components.

Due to the worldwide distribution of vaccines and the diversity of ambient temperatures, it is necessary to formulate vaccines such that they are stable under a variety of environmental conditions. A variety of stabilization methods have been used. These include the following:

a) Low temperatures (−10° C. to −70° C. ). Most vaccines are stable during storage at extremely low temperatures. However, low temperature storage facilities are costly and are not always available; this limits the utility and practicality of this approach.

b) Lyophilization. Freeze-dried vaccines are reasonably stable and can be stored at 2–8° C. for a predefined length of time. Lyophilization may, however, result in a loss of viral titer during drying thereby reducing the yield of the manufacturing process. In addition, during long-term storage, a lyophilized vaccine may still deteriorate, to the point where it may or does not have sufficient titer to confer immunization. Furthermore, since a lyophilized vaccine requires reconstitution prior to use, a liquid reconstituted preparation may lose potency while standing at room temperature before use. This loss of titer during reconstitution may also result in insufficient titer to confer immunity.

c) Stabilizers. These are specific chemical compounds that interact and stabilize biological molecules and/or general pharmaceutical excipients that are added to the vaccine and are used in conjunction with either lower temperature storage or lyophilization methods.

These formulations can be prepared by either (1) dilution of bulk vaccine into the stabilizer, (2) dialysis/diafiltration into the stabilizer, or (3) concentration of bulk vaccine and diafiltration into the stabilizer, followed by lyophilization if required.

The amounts and concentrations of the components of the formulations described herein will be understood by those skilled in the art to refer to the gram/100 milliliters percentage when referring to lyophilized or liquid formulations. For example, a 10% concentration in a liquid formulation is 10 grams per 100 milliliters and a 10% concentration of a lyophilized formulation refers to 10 grams per 100 milliliters after reconstitution of the lyophilized formulation with an appropriate diluent. Other measures, such as the molarity of a compound, refer to a liquid formulation or to a lyophilized formulation after reconstitution with an appropriate diluent.

The stabilizer composition of the present invention contains the following ingredients in about the amounts indicated. For convenience the amounts are stated round numbers. However, one skilled in the art will recognize that amounts within 10 or 20 percent of the stated values can also be expected to be appropriate, i.e., where 20% is stated, a range of from 16–18% to 22–24% is implicit and can be appropriate.

| | |
|---|---|
| Sucrose: | 1–70% (w/v) |
| Sodium or potassium phosphate: | 0.01–2 M |
| Sodium succinate or sodium citrate: | 0.05–2 M |
| Tissue culture medium, saline, or water: | 0-balance of remaining volume |
| For lyophilized formulations: | |
| Sodium phosphate | 0.05–2 M |
| Sucrose | 1–20% (w/v) |
| Mannitol | 1–20% (w/v) |
| Lactose | 1–20% (w/v) |
| In addition, the following can also be present: | |
| Hydrolyzed gelatin | 2.5% (w/v) |
| Sodium chloride | 150 mM |
| Sodium glutamate | 7 mM |

The following compounds can be used in place of sucrose, and at comparable osmolality: fucose, trehalose, polyaspartic acid, inositol hexaphosphate (phytic acid), sialic acid or N-acetylneuraminic acid-lactose. Also, any suitable sugar or sugar alcohol such as dextrose, mannitol, lactose, or sorbitol, can be substituted for sucrose at concentrations effective in achieving the desired stabilization.

The concentration of sugar relates to the viscosity of the formulation. In instances where reduced viscosity is desired, it is known in the art to be preferable to use lower concentrations of sugar, e.g., sucrose. It will also be appreciated by persons in the art that the upper limit for the concentration of sugar can be dictated by the ability of a formulation to undergo required filtration or processing steps.

Another sugar compound that can be used to stabilize liquid embodiments of the vaccine formulations taught herein is polysorbate, a chain of multiple sorbose units. Liquid formulations are made as taught herein with the addition of polysorbate. Polysorbate can be obtained in a variety of chain lengths from. It is preferred that when adding polysorbate, a chain length between 20 and 80 units is employed. A concentration of about 0.01% to about 0.50% polysorbate 80 or polysorbate 20 in a liquid formulation is most preferred Amino acids can be employed in the lyophilized formulations taught herein. It has been found that some amino acids, particularly charged amino acids can improve the stability of a vaccine prepared in the lyophilized formulations. Preferred amino acids are arginine, glutamate and glutamine. A concentration of about 0.5% to about 2% dry weight is appropriate. A concentration of about 0.75% to about 1.25% dry weight is preferred and a concentration of about 1% dry weight is most preferred in lyophilized formulations. A combination of amino acids can be used but the overall concentration of the combined amino acids should be no more than 2.0%

Another excipient useful in both liquid and lyophilized formulations of vaccines as taught herein is recombinant human albumin. Recombinant human serum albumin is produced using gene expression systems and therefore is safer to use than albumin isolated from the serum of human beings. The concentration of the albumin is typically in the range of about 0.1 to about 2%, preferably about 1.0%.

Tissue culture medium, saline or water can be used as a diluent. Frequently, Williams' E medium ("WE") is used, by which we mean either Williams' E medium or Williams' medium E modified.

Also, buffering agents to neutralize gastric acid are not limited to citrate, phosphate and succinate and could include bicarbonate or common carboxylic acids (carboxylates) such as, but not limited to, fumarate, tartarate, lactate, maleate, etc. The appropriateness of any of these can be assessed by simply trying a formulation in which these agents are substituted or combined with phosphate, citrate or succinate. Up to about 2.0 M carboxylates can be used in the liquid and lyophilized formulations of this invention, however, we prefer to use less than about 1.0 M, e.g., about 0.05–0.9 M, and can be less than about 0.7 M, e.g., 0.05 to about 0.7 M. It is also preferable to use less than 0.5 M, e.g., about 0.05 to 0.45 M. Particular concentrations in these ranges can be appropriate. Also, higher concentrations of buffering components (e.g. phosphate, succinate, citrate) can be used if, for example, additional gastric neutralization is required. In instances where additional buffering capacity is useful in phosphate/citrate or phosphate/succinate buffers, it is preferable to further increase the concentrations of succinate or citrate as the buffering agent rather than phosphates.

Up to about 2.0 M phosphate can be used in the liquid and lyophilized formulations of this invention, however, we prefer to use less than about 1.0 M, e.g., about 0.010–0.8 M, and often less than 0.5 M, e.g., about 0.010 to 0.45 M. It is most preferable to use less than about 0.35 M, e.g., 0.010–0.30 M. Particular concentrations in these ranges can be appropriate. In liquid formulations, we prefer to maintain the concentration of phosphate about or below 0.30 M, e.g., 0.010–0.35 M to avoid the precipitation of phosphate salts, e.g., during long term storage or freeze/thaw cycles. Thus, the upper limit for the concentration of phosphate in any particular formulation can be dictated by the formation or precipitation of phosphate salts and whether the salts negatively affect the performance of the formulation in areas such as stability and administration. Particular concentrations can be readily determined for any particular formulation by standard empirical testing including pH adjustments in the range of pH 6–8.

For general guidance, examples of the acid neutralizing capacities of some liquid formulations are presented in Table 1 below. Also provided are some preferred formulations.

TABLE 1

Acid-neutralizing capacities (ANC) of rotavirus stabilizer formulations.

| Sodium Phosphate (M) | Sodium Citrate (M) | Sucrose (%) | ANC (mEq/mL) |
|---|---|---|---|
| 0.30 | 0.10 | 50 | 0.48 |
| 0.30 | 0.70 | 50 | 1.55 |
| 0.75 | 0.25 | 50 | 1.07 |

For lyophilized formulations:

| | |
|---|---|
| Sodium phosphate | 20 mM |
| Hydrolyzed gelatin | 2.5% (w/v) |
| Sucrose | 5% (w/v) |
| Sodium chloride | 150 mM |
| Sodium glutamate | 7 mM |
| or | |
| Sucrose or Lactose | 1% (w/v) |
| Mannitol | 4% (w/v) |
| Sodium or potassium phosphate | 0.01–0.1 M |

A preferred formulation of the liquid viral vaccine stabilizer of the resent invention is as follows:

| | |
|---|---|
| Sucrose | 50% (w/v) |
| Sodium or potassium phosphate | 0.1 M |
| Sodium succinate | 0.2 M |
| Tissue culture medium | used for all dilutions |
| or | |
| Sucrose | 50% (w/v) |
| Sodium or potassium phosphate | 0.3 M |
| Sodium citrate | 0.1 M |
| Tissue culture medium | used for all dilutions |
| or | |
| Sucrose | 30% (w/v) |
| Sodium or potassium phosphate | 0.3 M |
| Sodium citrate | 0.7 M |
| Tissue culture medium | used for all dilutions |

In these preferred formulations, it can be appropriate to use saline or water in place of, or in combination with, the tissue culture medium.

This invention involves formulations of reassortant rotaviruses (RRV) suitable for use as vaccines, which are characterized by safety to humans and the ability to confer immune protection against human rotavirus infection. The RRV are produced by genetic reassortment between an attenuated bovine rotavirus (preferably WC3 or progeny thereof) and at least one rotavirus representing an epidemiologically important human serotype. In one type of RRV, the human rotavirus contributes to the reassortant at least the gene segment encoding the VP7 protein. In another type of RRV, the human rotavirus parent contributes to the reassortant at least the gene segment encoding the VP4 protein. In still another type of RRV, the human rotavirus parental strain contributes at least both the VP7 and VP4 gene segments. In additional types of RRV, the human rotavirus parental strain may contribute gene segments in addition to those which encode the VP7 and/or VP4 antigens.

The human rotavirus gene which encodes for the neutralization antigen VP7 and/or VP4 in the RRV may be selected from any human rotavirus serotype for which immunization is desired. Desirably, in a reassortant of this invention the VP7 gene is derived from a G1, G2, G3, or G4 human rotavirus serotype and the VP4 protein is derived from a human P1 or P2 serotype. Among the rotavirus strains noted to be clinically significant in human rotavirus infections (hereinafter "human rotavirus strains"), including strains useful in the present invention, are the strains provided below:

serotype G1: WI79, Wa, D;

serotype G2: strains WISC2 and DS1;

serotype G3: strains WI78, P, HCR3A;

serotype G4: Bricout (Br) B, ST3;

serotype G8: 69M;

serotype G9: WI61;

serotype P1: WI79, WI78, WI61, Wa;

serotype P2: DS1; and serotype P3: WISC2, BrB, BrA, M37.

This list of human rotavirus strains is non-exclusive. For example, several rotavirus strains previously identified in animal infections have also been found in human infections. These strains can be anticipated to be useful as 'human' rotavirus strains for the purposes of this invention, e.g., the 'porcine' rotavirus OSU, a serotype G5, and the 'bovine' rotavirus B223, a serotype G10. One of skill in the art can readily obtain other appropriate human strains from suitable depositories or academic or commercial sources.

The non-human genes present in the reassortants of this invention are obtained preferably from the attenuated, serotype G6, bovine rotavirus strain WC3 or its progeny, described in detail in U.S. Pat. No. 4,636,385. However, other rotavirus reassortants, particularly other bovine reassortants, are also preferred.

TABLE 2

| Human Serotype | Parent or Reassortant | ATCC # | Deposit Date |
|---|---|---|---|
| G1 | WI79-3,9[a] | VR2194 | Nov. 25, 1987 |
| | | VR2196 | Nov. 25, 1987 |
| | WI79-4,9 | VR2415 | July 8,1993 |
| G2 | WI79-3 + WISC2-9 | | Dec. 7, 1994 |
| | WISC2 parental strain | VR2417 | July 8, 1993 |
| G3 | WI78-8 | | Dec. 7, 1994 |
| | WI78-1,6-11 | VR2195 | Nov. 25, 1987 |
| | WI78-1,7-11[b] | | |
| G4 | Bricout B-9 | | Dec. 7, 1994 |
| P1 | WI79-4 | VR2377 | June 19, 1992 |
| | WI79-4,9 | VR2415 | July 8, 1993 |
| | WI61-4[b] | | |
| P2 | DS1-4[b] | | |

[a]Originally named WI79-9. The two deposits represent different passage levels of the reassortant.
[b]Not deposited.

It is understood that the strains listed in Table 2 have been deposited under the Budapest Treaty in reference to U.S. Pat. Nos. 5,626,851 & 5,750,109.

Vaccine Compositions

Vaccines for providing immunological protection against acute diarrhea caused by human rotavirus infection can contain one or more rotavirus reassortants in a formulation of the present invention. Exemplary rotavirus reassortants and combinations thereof and their use in vaccines are found in U.S. Pat. Nos. 5,626,851 and 5,750,109, both of which are incorporated herein by references in their entireties. Several exemplary vaccine compositions are summarized in Table 3.

TABLE 3

| Vaccine compositions | Preferred Reassortants |
|---|---|
| G1 + G2 + G3 + G4 | WI79-3,9 + (WI79-3 + WISC2) + WI78-8 + BrB-9 |
| G1 + G2 + G3 + G4 + P1 | WI79-3,9 + (WI79-3 + WISC2-9) + WI78-8 + BrB-9 + WI794 |
| G1 + G2 + G3 + P1 | WI79-3,9 + (WI79-3 + WISC2-9) + WI78-8 + WI79A |
| G1 + P1 | WI79-3,9 + WI79-4 |
| G1 + G2 + G3 | WI79-3,9 + (WI79-3 + WISC2-9) + WI78-8 |
| G1 + G2 + G3 + G4 + P1 + P2 | WI79-3,9 + (WI79-3 + WISC2-9) + WI78-8 + BrB-9 + WI794 + DS1-4 |
| G1 | WI79-3,9 |

The rotavirus vaccines of the invention can contain conventional components. Suitable components are known to those of skill in the art. These vaccine compositions can be prepared in liquid forms or in lyophilized forms. Other optional components, e.g., stabilizers, buffers, preservatives, flavorings, excipients and the like, can be added. The determination of specific formulations useful in stabilizing vaccine compositions has required extensive experimentation.

When adapted for oral administration, one formulation includes as a carrier Williams' E medium ("WE")/50% sucrose/0.1 M succinate/50 mM phosphate liquid. Other formulations include 0.2 M succinate and 0.1 M phosphate, or 0.1 M citrate and 0.3 M phosphate. Another formulation includes 0.7 M citrate and 0.3 M phosphate with Williams' E medium/30% sucrose. In addition, novel adjuvants to boost or augment immune responses developed for oral administration should be compatible with these formulations. When adapted for parenteral administration, conventional adjuvants (e.g., aluminum salts) or novel adjuvants can also be employed in the vaccine composition.

Optionally, the vaccine may preferably be formulated to contain other active ingredients and/or immunizing antigens. For example, when adapted for oral administration, formulation with the Sabin polio vaccine may be desirable.

The dosage regimen involved in a method for vaccination, including the timing, number and amounts of booster vaccines, will be determined considering various hosts and environmental factors, e.g., the age of the patients time of administration and the geographical location and environment.

Method of Vaccination

Therefore, also included in the invention is a method of vaccinating humans against human rotavirus infection with the novel RRV vaccine compositions. The vaccine compositions including one or more of the reassortants described herein are administered, preferably by the oral route, in a suitable dose, preferably liquid.

The dosage for all routes of administration is generally between $10^5$ and $10^9$ plaque forming units (pfu) of the reassortant with the preferred dosage being $10^7$ pfu. Additional doses of the vaccines can be also be administered. It may be preferable to inoculate susceptible infants and children on an annual basis prior to the "rotavirus season". Rotavirus infection in humans has been observed to occur in various geographical regions during the same season, e.g., in winter in the United States. Repeated inoculations prior to that season for susceptible infants and children may be indicated. For example, one currently preferred dosage regimen for the U.S. includes three doses approximately two months apart prior to the beginning of the rotavirus season.

The following examples illustrate methods for preparing the RRV vaccine formulations of the invention. These examples are illustrative only and do not limit the scope of the invention.

EXAMPLE 1

Administration of a vaccine by the oral route exposes the vaccine to the low pH gastric environment. Most vaccines tend to be inactivated by such extreme conditions. In order to ensure delivery of active vaccine, potential buffers were examined for acid neutralizing capacity as well as their ability to stabilize rotavirus.

Rotavirus Stability in the Presence of Acid Neutralizing Buffers

Citrate, lactate, and succinate buffer combinations (5 total) were evaluated for their effect on rotavirus stability at 37° C. over a 1 week period. The buffers, whose concentrations are given in the legend to FIG. 1, were added to an equal volume of rotavirus in WE medium and incubated for 0, 3, or 7 days.

For the G1 serotype, the bicarbonate combinations had no effect on the time to lose one half of the infectious titer ($t_{1/2}$) since the values were similar to those in 5% sucrose (0.5 days). In contrast, the phosphate buffers containing citrate, lactate, and succinate stabilized the virus exhibiting $t_{1/2}$ values of 1.2, 1.4, and 1.5 days, respectively (FIG. 1).

Figure 1B:
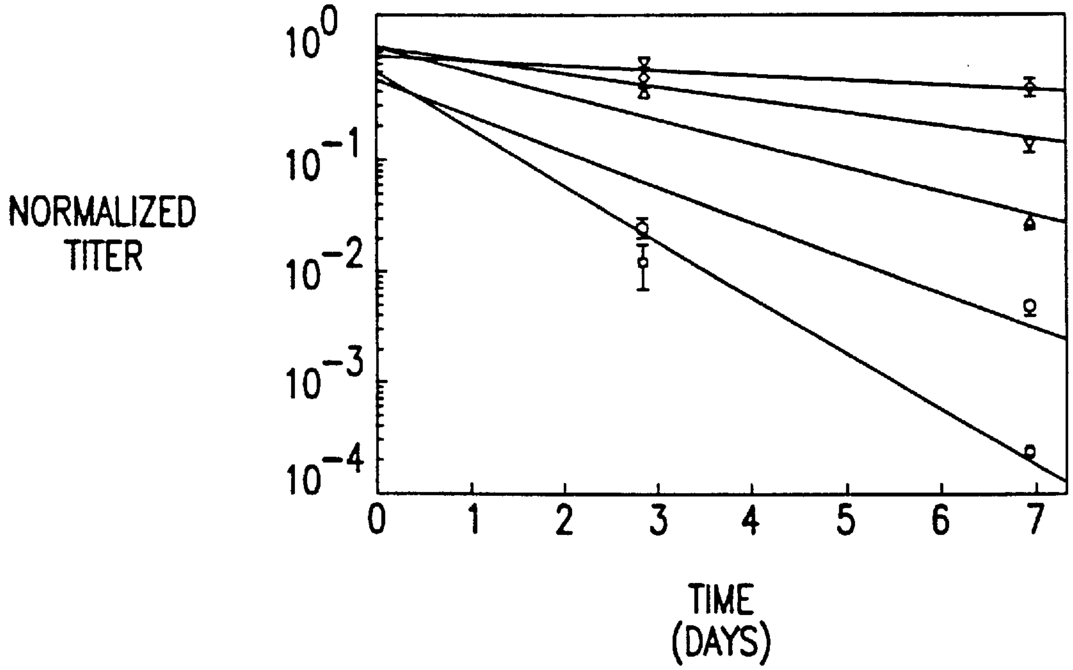

As shown in FIG. 1, phosphate had a similar effect on the stability of P1. The lactate/phosphate buffer had a $t_{1/2}$ of 2.4 days, and the succinate/phosphate combination had a $t_{1/2}$ of 6.8 days compared to a value of ca. 1.2 days for a 5% sucrose solution. Similar to their effect on the G1 rotavirus, the buffer combinations containing bicarbonate conferred less stability on the P1 serotype than similar buffers containing phosphate.

Figure 2:
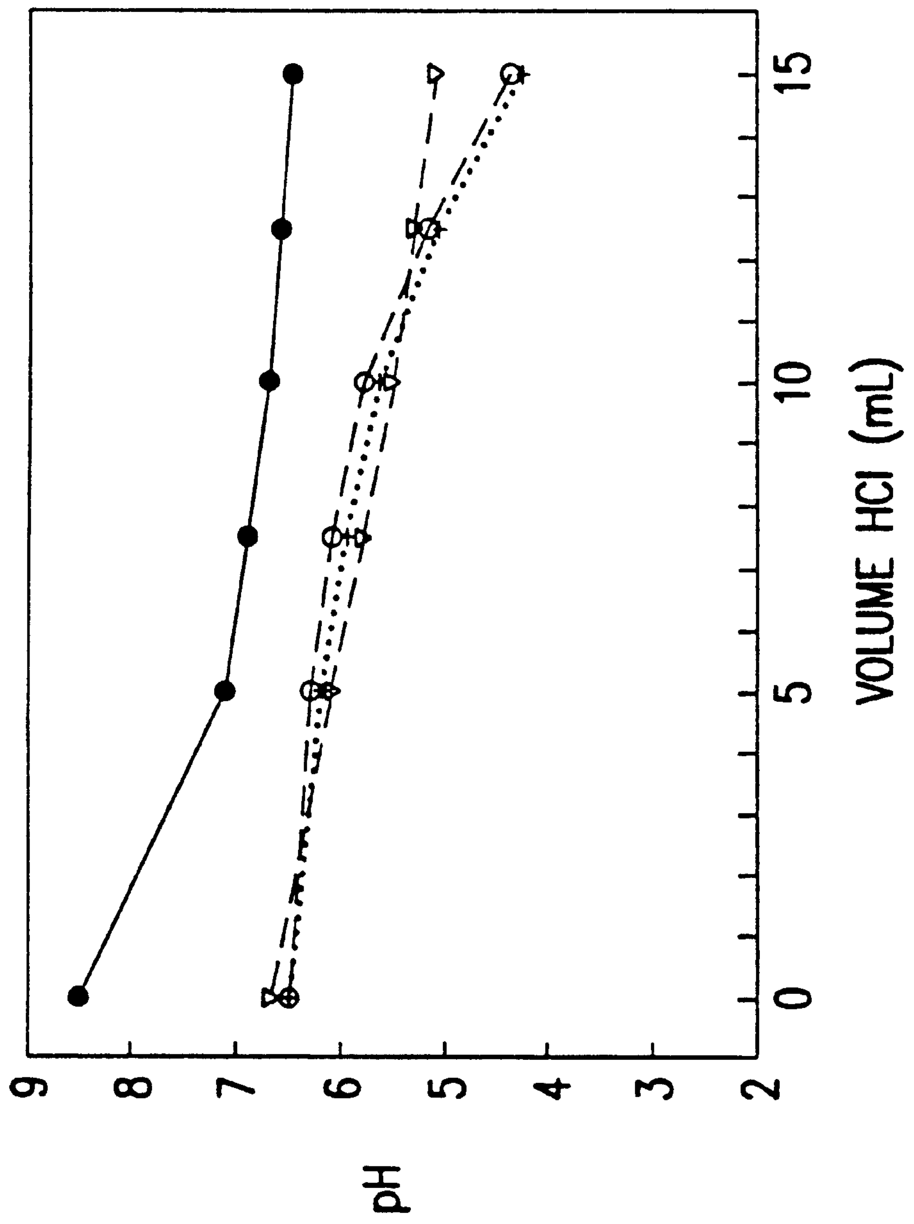
FIG. 2. Acid neutralizing ability of formulation buffers compared to bicarbonate. One mL of each buffer was titrated with 0.01 N HCl. Symbols: 0.4 M sodium bicarbonate (●), 0.1 M sodium citrate+0.3 M sodium phosphate (○), 0.1 M sodium citrate+0.3 M sodium bicarbonate (+), and 0.2 M sodium succinate+0.1 M sodium phosphate (▽).

Combination of Rotavirus with Acid Neutralizing Buffer-Potential Single Administration The stabilizing effect of succinate/phosphate as well as other buffers suggests that the formulation can contain an acid neutralizer. One mL of the buffers tested appear to neutralize enough acid to keep the pH above 3.5 (FIG. 2) which is known from our direct experimentation and the scientific literature to be necessary for preservation of rotavirus infectivity. Based on infant gastric acid volumes and acid secretion rates, the pH can be maintained in vivo for approximately 0.5 h with the liquid formulations to be described in this work, however, human clinical studies will have to be performed to confirm these assumptions. As another test of buffering ability, the USP test for acid-neutralizing capacity was performed. As shown in Table 4, RV formulation buffering components are more effective than an equal volume of infant formula.

TABLE 4

Acid-neutralizing capacity as measured by USP test for a novel liquid rotavirus formulation (1); formulation used in previous clinical trials by others (2); tissue culture media (3); infant formula (4), and an antacid (5).

| | mEq/mL |
|---|---|
| (1) 50% sucrose + 0.2 M sodium succinate + 0.1 M sodium phosphate in Williams' E media ("WE") | 0.41 |
| (2) 0.3 M sodium bicarbonate + 0.033 M sodium citrate | 0.40 |
| (3) Williams' E media | 0.02 |
| (4) Isomil ® | 0.12 |
| (5) Mylanta ® | 5.17 |

For lyophilized formulations, additional buffering capacity can be attained by reconstitution with an acid-neutralizing buffer described in this work or commonly available acid neutralizing compounds such as a bicarbonate solution. Thus, with either a liquid or lyophilized formulation, adequate buffering capacity is possible without pretreatment. Consequently, the rotavirus vaccine may preferably be able to be administered in a single administration rather than with a separate gastric neutralization step followed by the vaccine. However, simultaneous administration of buffer and vaccine will have to be further evaluated in patients to have confidence in the efficacy of the vaccine using in this approach. If pretreatment of patients (formula feeding or dose of bicarbonate or an antacid such as Mylanta®) is still necessary to ensure adequate gastric acid neutralization for routine oral vaccination with rotavirus, these formulations will still provide a large enhancement in the storage stability as described in the next section. Furthermore, the rotavirus reassortants are compatible with infant formulae (e.g., Isomil® and Similac®) as well as bicarbonate buffers and show comparable thermal stability in the presence or absence of these neutralizers.

EXAMPLE 2

Putative binding sites on rotavirus can be considered as targets for stabilization. Calcium and zinc binding sites have been suggested to be present in rotavirus proteins and the presence of these cations may stabilize the vaccine. Other divalent cations may also bind to these or other sites and stabilize rotavirus and its reassortants. Binding by other compounds was also investigated in order to identify compounds that can stabilize the vaccine yet not interfere with its ability to confer immunogenicity.

a. Effect of Divalent Metal Ions

The addition of metal chelators such as EDTA or EGTA is known to cause a loss in RV infectivity, presumably by disrupting the outer shell of the RV. This suggests that metals may be necessary for structural integrity. Accordingly, divalent metal ions were examined to assess their potential ability to stabilize rotavirus (RV).

Rotavirus in WE medium was dialyzed at 4° C. for approximately 16 hours in 20 mM Tris buffer and 100 mM NaCl. The final solution was supplemented with 10 mM of either $CaCl_2$, $MnCl_2$, $MgCl_2$, $ZnCl_2$, or $CaCl_2$+$ZnCl_2$ to yield a final concentration of 10 mM metal ion. The samples can be filtered prior to formulation. Samples were incubated at 37° C. for 0, 2/3, and 7 days and were then stored at −70° C. until assayed. Each data point represents an average of 2 replicate samples.

As shown in Table 5, calcium and manganese do improve the stability of both G1 and P1 rotavirus reassortants at 37°

C. when the formulations are prepared by dialysis of the rotavirus bulks into formulations without tissue culture medium. Zinc dramatically decreased the inactivation half-life ($t_{1/2}$) of G1 and significantly decrease the $t_{1/2}$ of P1 in the presence or absence of calcium. It is possible that $Zn^{2+}$ may be replacing $Ca^{2+}$, causing the destabilization of the outer capsid in a manner analogous to the removal of $Ca^{2+}$ by EDTA. An alternative explanations may be that $Zn^{2+}$ activates endogenous metalloproteinases or potentiates nucleases derived from the cell culture. The addition of divalent metals does not increase the thermal stability of RV when formulated in a stabilizer containing tissue culture medium such as Williams' E or Williams' modified E. The G2 and G3 reassortants appeared to behave similarly to G1 and P1 reassortants when compared in cation-supplemented tissue culture media.

Thus, in preparing stabilized formulations of rotaviruses as described herein, it is preferable that sufficient levels of divalent metal ions be present. These metal ions are most likely provided by the tissue culture medium and cells used in cell culture to prepare the bulk virus. Metal ions can also be supplemented, if necessary, in the final formulation by direct addition individually or through the use of tissue culture medium.

TABLE 5

Effect of divalent metals on the inactivation kinetics of rotavirus reassortants. Values represent the log loss in viral titer after 3 days at 37° C.

| Cation (10 mM) added | P1 | G1 |
|---|---|---|
| none | 2.2 | 2.5 |
| $Ca^{2+}$ | 0.5 | 0.2 |
| $Zn^{2+}$ | >3.8 | >4.0 |
| $Zn^{2+}$ + $Ca^{2+}$ | >3.9 | >3.9 |
| $Mn^{2+}$ | 1.5 | 2.2 |
| $Mg^{2+}$ | 2.6 | 4.2 |

b. Effect of Biologically Relevant Sugars and Polyanions

Preliminary experiments described above showed rotavirus reassortants are stabilized by phosphate buffer. Since there are examples of monomeric proteins which are stabilized by phosphate that are also stabilized by related polyanions such as sulfate, inositol hexaphosphate (phytic acid) and various sulfated compounds (heparin and sulfated β-cyclodextrin), these compounds were tested for their ability to stabilize rotavirus. Polymeric forms of polyanions are generally more effective stabilizers since a higher charge density can be maintained at lower concentrations of ligand, therefore, polyaspartic acid was also examined due to its high negative charge density. Sialic acid (N-acetylneuraminic acid) was examined since it may bind to VP4 and, therefore, may provide protection from thermally-induced degradation or unfolding. Likewise, sialic acid derivatives such as N-acetylneuraminic acid-lactose and mucin were tested. The loss of RV infectivity with host maturation has been suggested to be due to a switch in the presence of sialic acid to fucose; consequently fucose was examined. Lastly, trehalose was examined because of its reputed properties as a favorable drying excipient.

As can be seen in Table 6, a variety of compounds can be added to rotavirus formulations and stabilize the virus during accelerated stability testing. Inositol hexaphosphate showed the greatest ability to stabilize RV compared to the other ligands in this study. For G1, a 4-fold increase in thermal stability at 37° C. was observed. Mucin prevents infectivity, probably not by destabilizing the virion structure but rather sequestering RV (clumps were observed prior to assay). The sulfated polymers had a negligible effect, however, all other tested compounds stabilized RV to varying degrees. For example, trehalose extended the inactivation half-life for G1 by greater than 2-fold and P1 by less than 50%.

Sialic acid stabilized both G1 and P1 RV. Sialic acid should stabilize the G types and not the P types if the binding site is located on VP4. In these experiments, P1 appeared to have a lower half-life in the presence of polyanions in general. The lower $t_{1/2}$ in the presence of heparin and polyaspartic acid may suggest that RV bind more tightly to these ligands rather than being destabilized by them. The mechanism of stability suppression is not entirely clear. A low level of infectivity as measured by the plaque assay can be caused by destabilization of the virion itself or sequestration of RV by the ligand. If the association between RV and the excipient is moderate, the ligand would be expected to dissociate under the diluted conditions of the assay (as well as in vivo). Tightly bound complexes can contain stable viral particles, yet are not infectious since they are unable to dissociate. This latter case appears to apply to mucin, heparin, and possibly polyaspartic acid. Also, adverse effects of the excipients on the cells used in the plaque assay cannot be disregarded. Regardless of the mechanism, certain polyanions provide no advantage. Inositol hexaphosphate appears to be the most favorable of all the ligands examined, exceeding the stability induced by phosphate-containing buffers. These results also support previous studies described in this work which show phosphate dramatically stabilizes RV. Thus, a variety of phosphates (e.g., monophosphates and polyphosphates) and phosphorylated compounds (e.g., phosphorylated sugars) can stabilize rotavirus.

TABLE 6

Effect of polyanions and sugars on the inactivation kinetics. Samples were incubated at 37° C. for 1 week.

| added to RV in WE | $t_{1/2}$ (days) for G1 | $t_{1/2}$ (days) for P1 |
|---|---|---|
| 5% sulfated β-cyclodextrin | 0.5 | 0.8 |
| 5% fucose | 1.2 | 1.7 |
| 5% poly-aspartic acid | 1.5 | 0.6 |
| 1% inositol hexaphosphate | 2.0 | 3.2 |
| 1% heparin | 0.7 | <0.1 |
| 1% sialic acid | 0.8 | 1.4 |
| 1% N-acetylneuraminic acid-lactose | 1.2 | 1.5 |
| 1% mucin | <0.1 | <0.1 |
| 5% trehalose | 1.3 | 2.0 |
| 5% sucrose | 0.5 | 1.4 |

EXAMPLE 3

One-year probe stability data were obtained for several optimized lyophilized and liquid formulations of G1 and P1 rotavirus at various temperatures and compared to the stability data of an unoptimized formulation, WE medium/5% sucrose. Optimized liquid formulations containing rotavirus reassortants in WE medium containing sucrose, sodium phosphate, and sodium succinate or sodium citrate showed a substantial improvement in stability. Further improvements in storage stability were observed for lyophilized formulations. With the appropriate formulation, the thermostability of rotavirus exceeds that of existing live-virus liquid (i.e., OPV) and lyophilized (e.g., measles) vaccines.

The stabilizing effect of either the succinate/phosphate or the citrate/phosphate buffers offers the potential of combining stability enhancement with a gastric neutralization. Liquid formulations as well as lyophilized formulations that can be reconstituted using this buffer can allow the formulation to be delivered in a single administration.

a. Liquid Formulation Stability Data

Figure 3A:
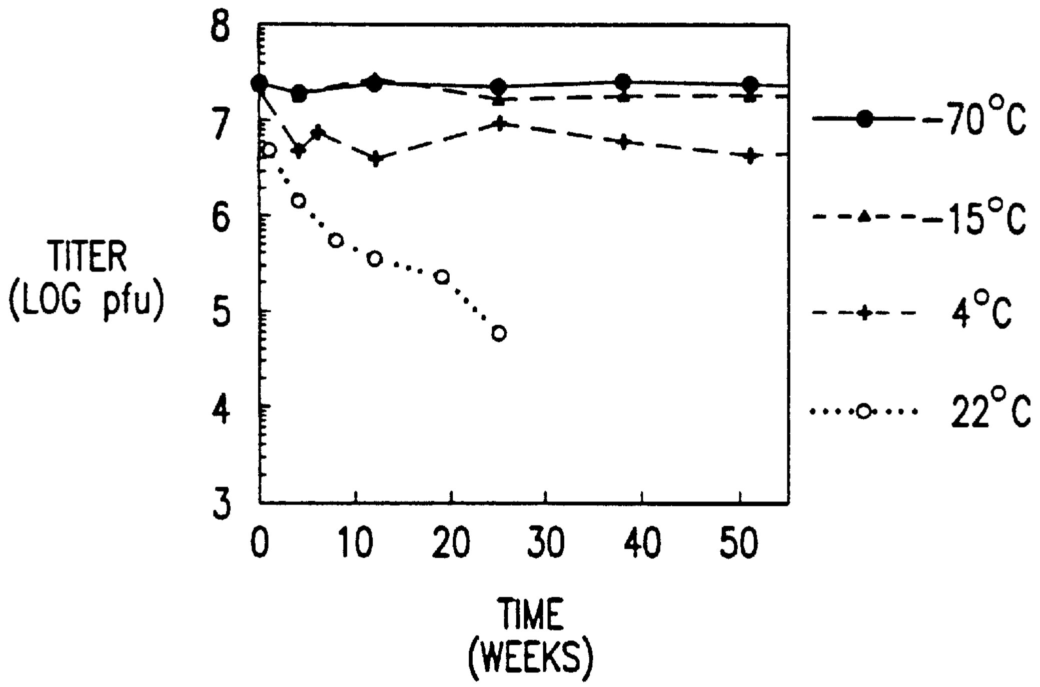
FIG. 3. Stability data for reassortant rotavirus in liquid formulations of 5% sucrose/0.1 M sodium succinate/0.05 M sodium phosphate after storage at various temperatures. Data for G1 rotavirus is shown in panel A and for P1 rotavirus in panel B.
Figure 3B:
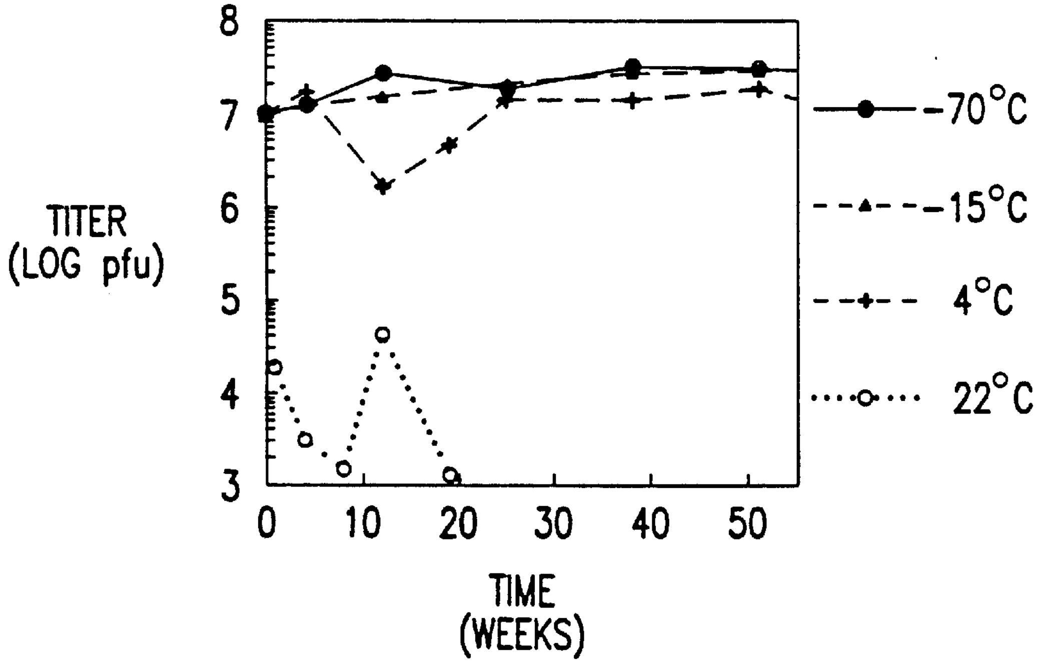

When formulated in Williams' E medium/5% sucrose/0.1 M succinate/50 mM phosphate at pH 7, the G1 rotavirus reassortant vaccine loses 0.7 log titer after 1 year at 4° C. when compared to samples stored at −70° C. (FIG. 3). The P1 reassortant vaccine loses 0.2 log under the same conditions. After 6 months at 22° C., the G1 reassortant lost 2.6 logs of infectious titer while the P1 reassortant rotavirus lost 5.2 logs. This can be compared to the unoptimized liquid formulation of the G1 reassortant in Williams' E medium/5% sucrose that was recently used in clinical trials which lost greater than 5 logs of infectivity after incubation for 6 months at 22° C. and 1–2 logs at 4° C. after one year. These data demonstrate the additional stabilizing effect of the specific buffer combinations described in this work.

Figure 4A:
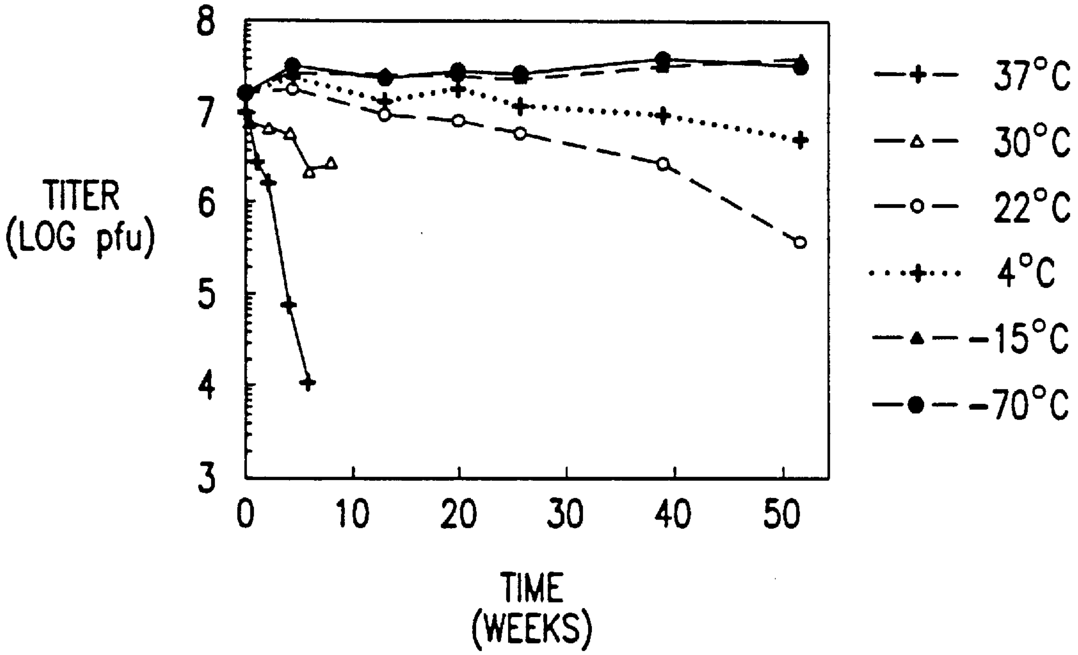
FIG. 4. Stability data for reassortant rotavirus in liquid formulations of 50% sucrose/0.1 M sodium succinate/0.05 M sodium phosphate after storage at various temperatures. Data for G1 rotavirus is shown in panel A and for P1 rotavirus in panel B.
Figure 4B:
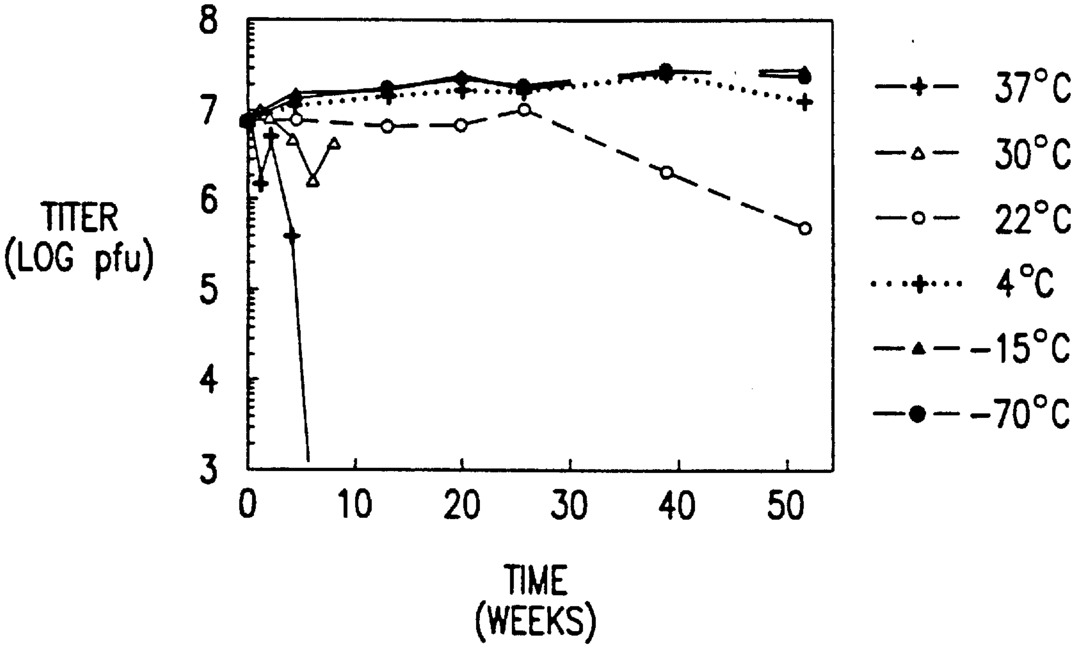
Figure 5A:
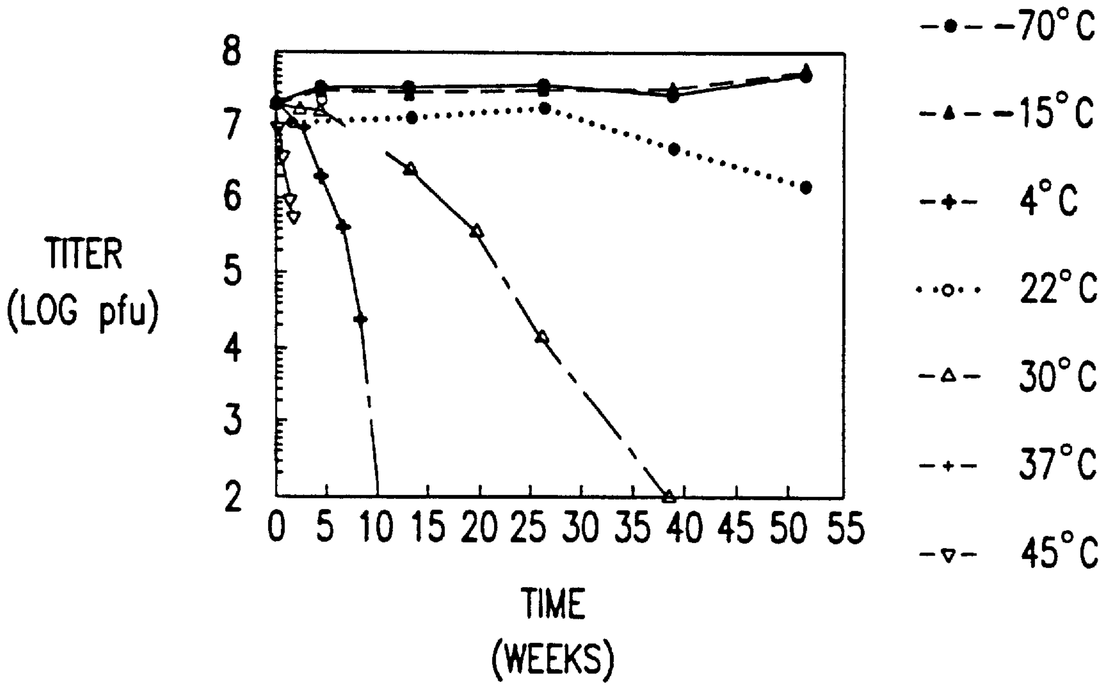
FIG. 5. Stability data for G1 rotavirus liquid formulations with higher buffer, sucrose, and hydrolyzed gelatin concentrations at various temperatures. Panel A shows data for G1 rotavirus in Williams' E media ("WE"), 50% sucrose, 0.2 M sodium succinate, and 0.1 M sodium phosphate. Stability data for vaccine in Williams' E media, 70% sucrose, 0.2 M sodium succinate, and 0.1 M sodium phosphate is shown in panel B. Panel C shows data for G1 rotavirus in 50% sucrose, 0.1 M sodium citrate, and 0.3 M sodium phosphate; panel D shows data for G1 rotavirus in Williams' E media, 50% sucrose, 0.2 M sodium succinate, 0.1 M sodium phosphate, and 5% hydrolyzed gelatin.
Figure 5B:
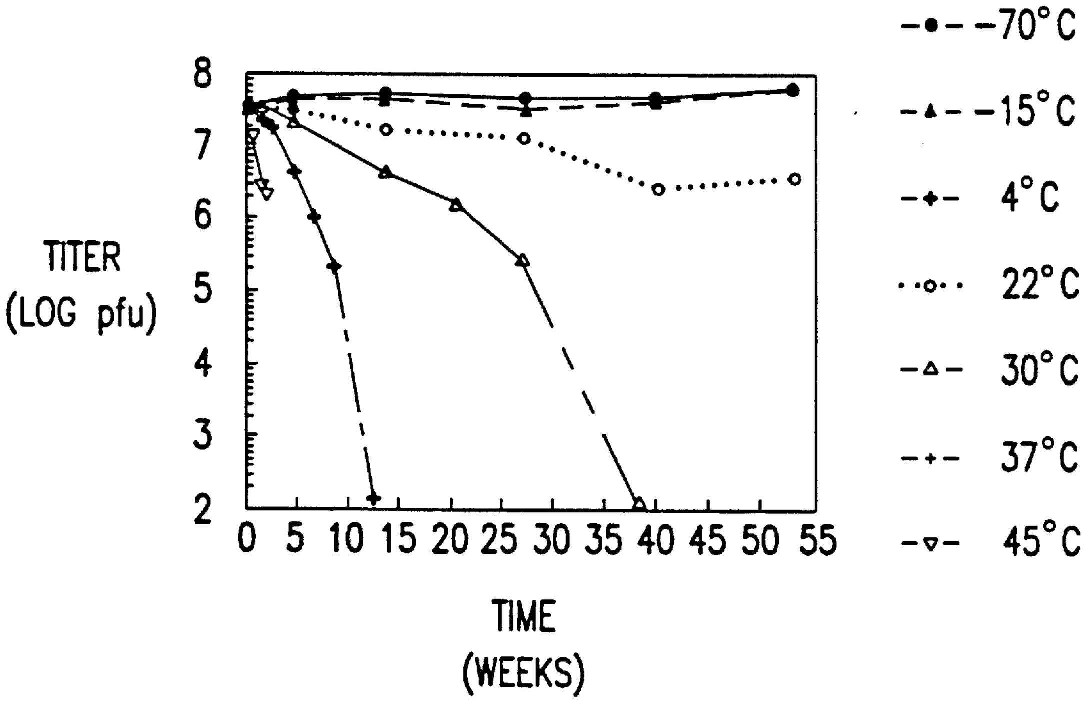
Figure 5C:
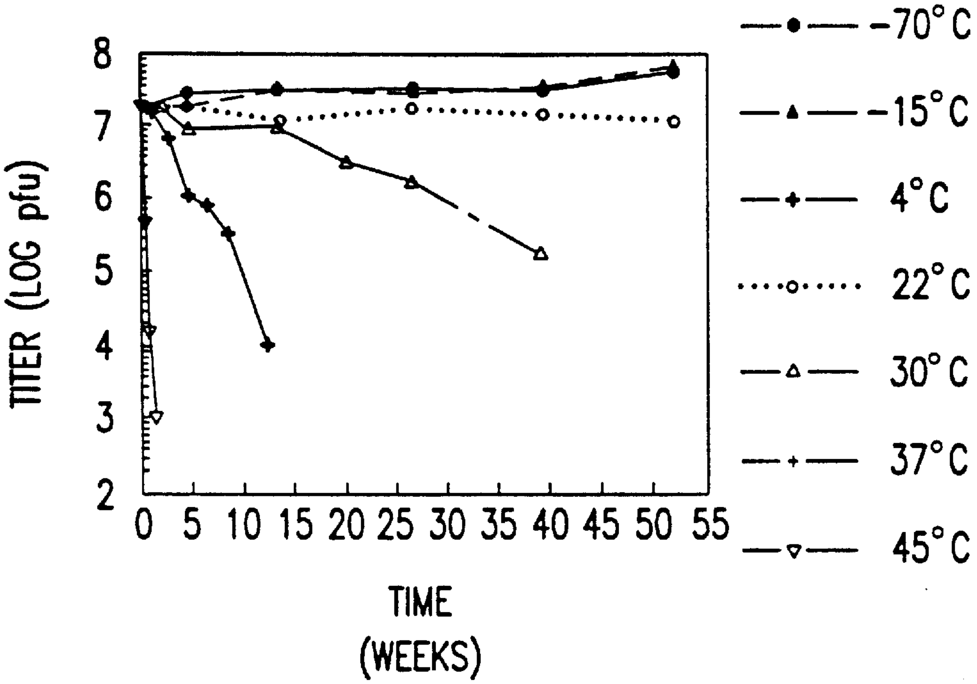
Figure 5D:
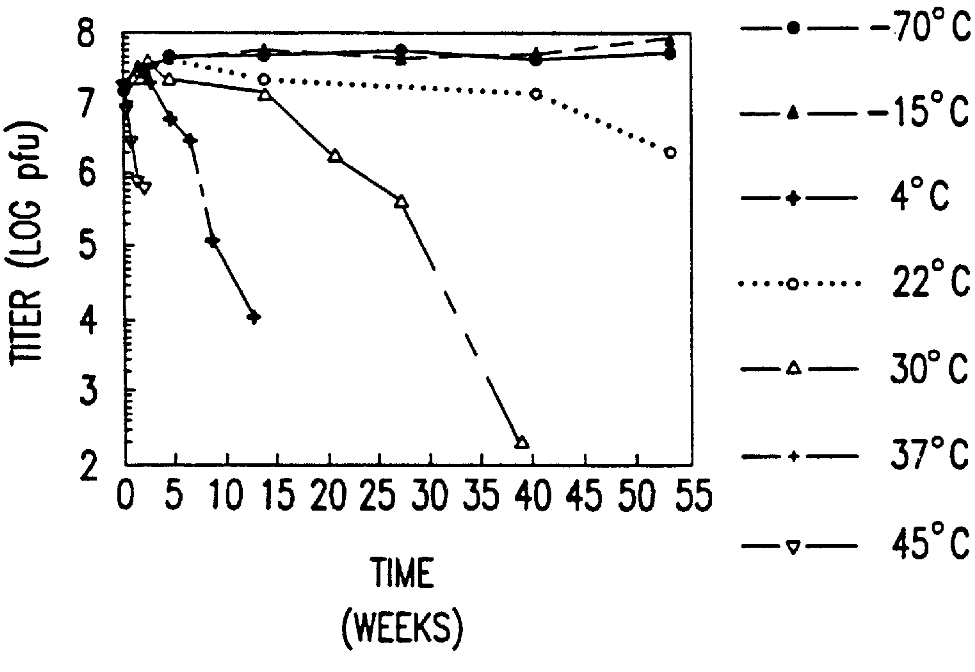
Figure 6A:
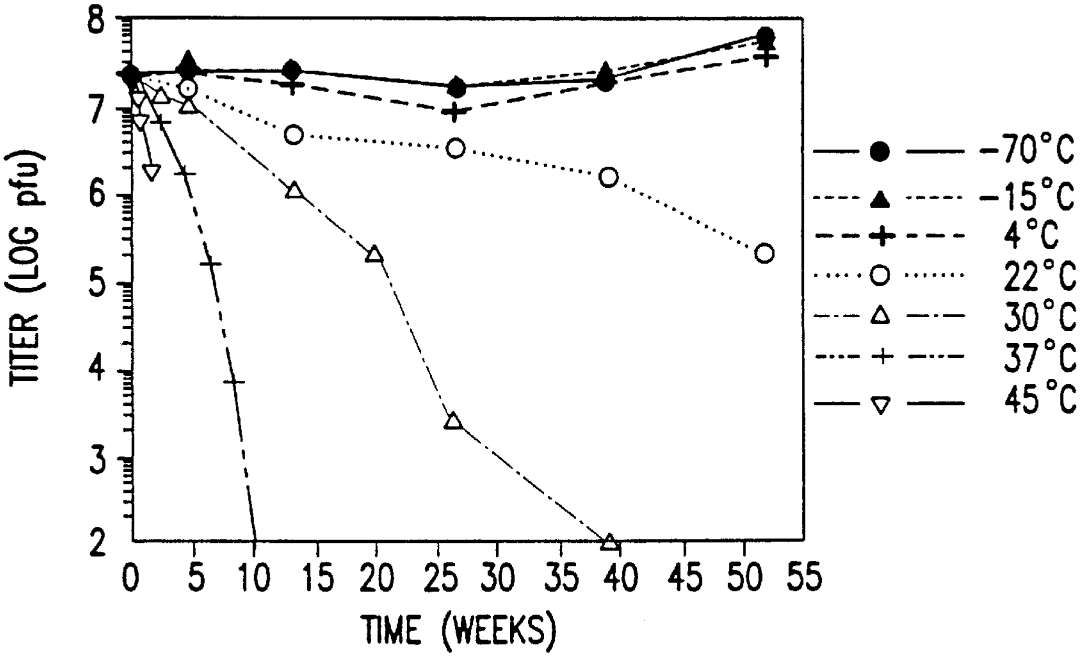
FIG. 6. Stability data for P1 rotavirus liquid formulations with higher buffer, sucrose, and hydrolyzed gelatin concentrations at various temperatures. Panel A shows data for P1 rotavirus in Williams' E media, 50% sucrose, 0.2 M sodium succinate, and 0.1 M sodium phosphate. Stability data for vaccine in Williams' E media, 70% sucrose, 0.2 M sodium succinate, and 0.1 M sodium phosphate is shown in panel B. Panel C shows data for P1 rotavirus in 50% sucrose, 0.1 M sodium citrate, and 0.3 M sodium phosphate; panel D shows data for P1 rotavirus in Williams' E media, 50% sucrose, 0.2 M sodium succinate, 0.1 M sodium phosphate, and 5% hydrolyzed gelatin.
Figure 6B:
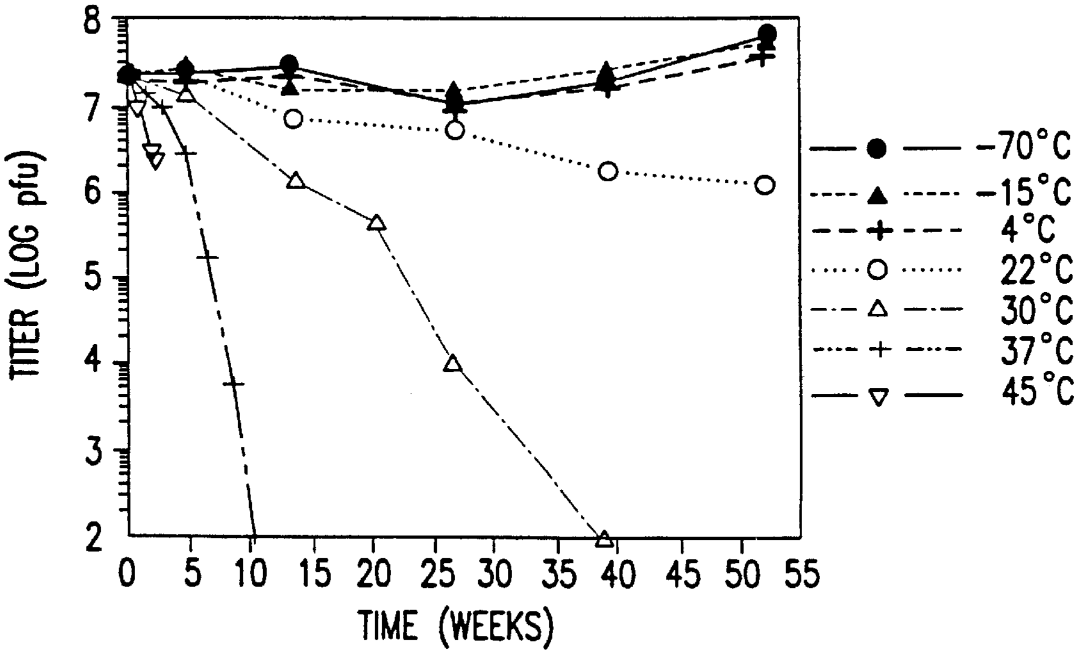
Figure 6C:
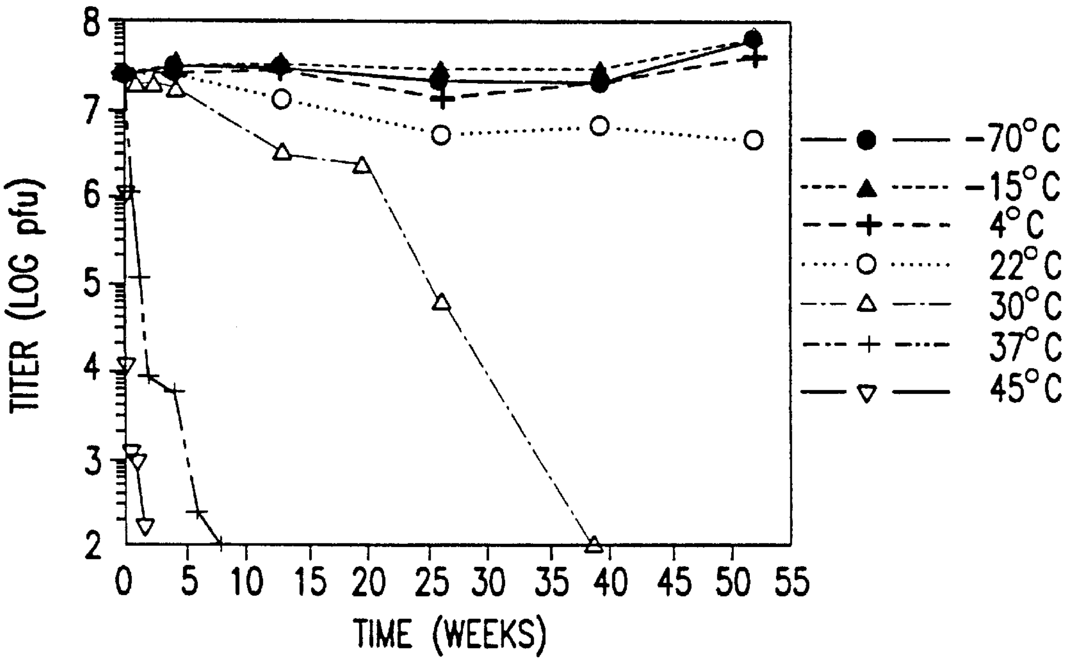
Figure 6D:
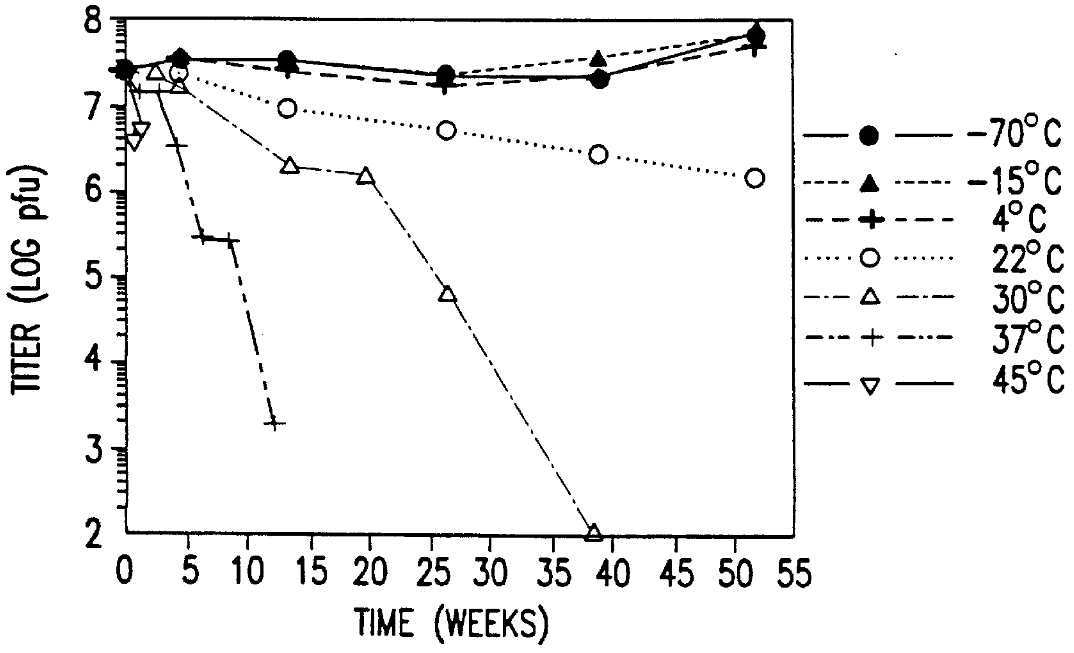

In Williams' E medium/50% sucrose/0.1 M succinate/50 mM phosphate at pH 7, the G1 rotavirus reassortant vaccine loses 0.8 logs titer after 1 year at 4° C. when compared to samples stored at −70° C. (FIG. 4). The P1 reassortant vaccine loses less than 0.3 logs under the same conditions. At 22° C., both G1 and P1 vaccines lose about 2 logs of infectivity after 1 year. These data demonstrate the additional stabilizing effect of high sugar concentrations.

Additional formulations with higher buffer concentrations (Williams' E medium/50% sucrose/0.2 M succinate/0.1 M phosphate, pH 7) further stabilize the G1 rotavirus vaccine at 4° C. resulting in no significant loss of titer when compared to similar samples stored at −70° C. (FIG. 5). Moreover, no loss in G1 titer is observed for any of the optimized liquid formulations stored at 4° C. for one year. The infectivity of the P1 reassortant is 0.2 logs less than the −70° C. samples for all formulations (FIG. 6). Although the stabilities of both G1 and P1 rotavirus reassortants at 4° C. are similar for formulations using higher buffer concentrations, the formulation containing Williams' E medium/50% sucrose/0.1 M citrate/0.3 M phosphate at pH 7 shows less loss at 22° C. when compared to other formulations. For example, G1 rotavirus in Williams' E medium/50% sucrose/0.2 M succinate/0.1 M phosphate shows a 1.5 log loss in titer after one year at 22° C., whereas the Williams' E medium/50% sucrose/0.1 M citrate/0.3 M phosphate formulation shows only a 0.6 log loss after this period. The higher phosphate concentration in the latter formulation can be responsible for the increased stability since the presence of phosphate and phosphorylated compounds increase the thermostability of rotavirus reassortants as demonstrated by our earlier screening experiments. Although rotavirus in the citrate/phosphate buffered formulation appears to be more stable at 22° C., it is less stable at 45° C. for both reassortants and at 37° C. for P1 rotavirus.

Figure 7A:
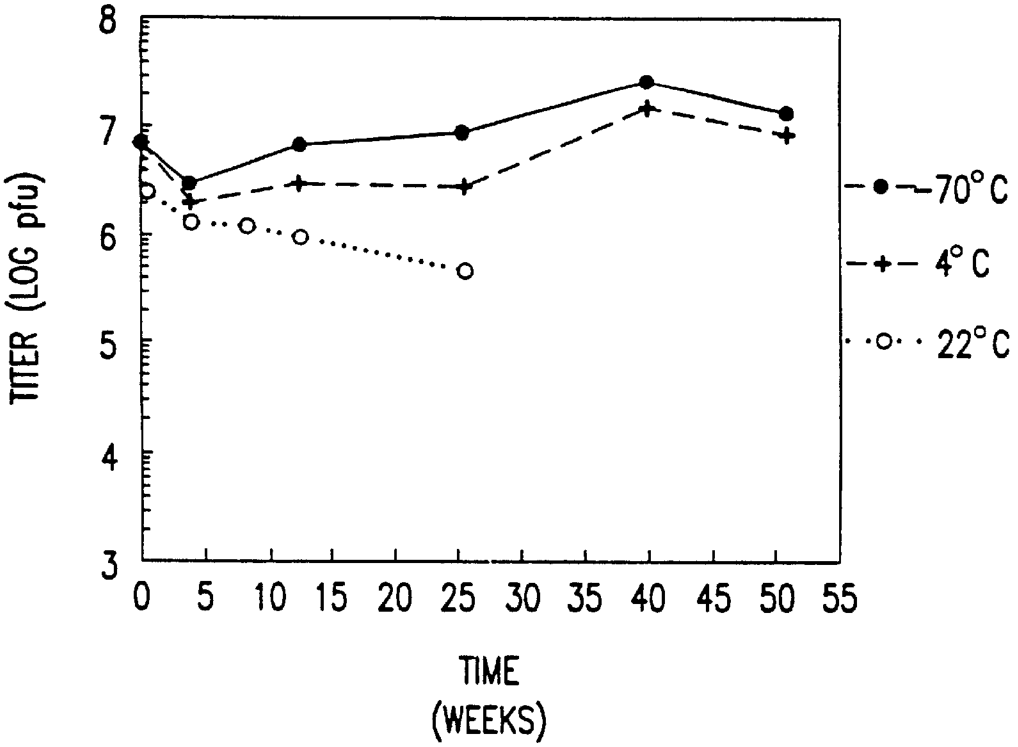
FIG. 7. Stability data for rotavirus liquid formulations in 50% sucrose, 0.1 M sodium succinate, and 0.05 M sodium phosphate after storage at various temperatures. Data for G2 rotavirus is shown in panel A and for G3 in panel B.
Figure 7B:
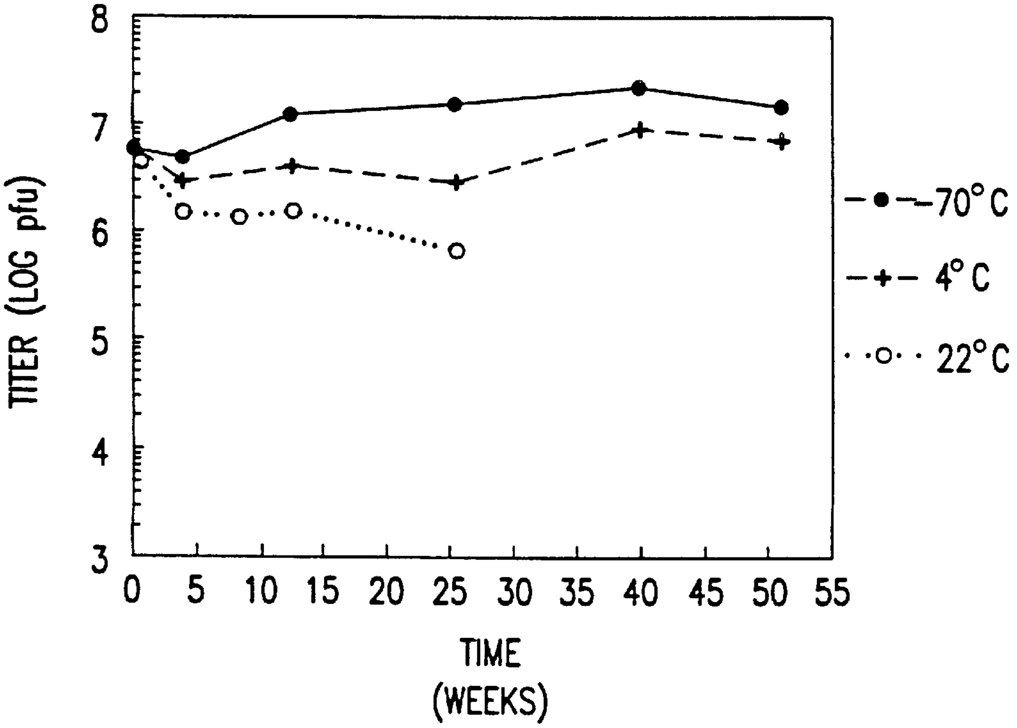

After 12 months at 4° C. in Williams' E medium/50% sucrose/0.1 M succinate/50 mM phosphate at pH 7, the G2 rotavirus reassortant lost 0.2 log of infectivity and the G3 reassortant decreased in titer by 0.3 log when compared to similar samples stored at −70° C. (FIG. 7). Compared to G1 and P1 reassortants in similar formulations (FIG. 3), G2 and G3 have stabilities comparable to that of the P1 rotavirus reassortant and better than that seen with the G1 reassortant at 4° C. However, the G2 and G3 vaccines appear to be less stable than the G1 vaccine at 22° C.

The stability of G1 reassortants was studied in the presence and absence of tissue culture medium in formulations including sucrose, phosphate and citrate (Table 7). Formulation A, containing only 5% sucrose in WE, served as the standard in this study. Test formulation B contains 0.3 M sodium phosphate and 0.1 M sodium citrate with 50% sucrose in WE. Test formulation C contains 50% sucrose, 0.3 M sodium phosphate and 0.1 M sodium citrate without WE. The viral bulk is diluted 10-fold into formulations B or C. Thus, 100% of the liquid medium in B is tissue culture medium whereas 10% of the liquid medium in C is tissue culture medium. In C, the viral bulk is the only source of tissue culture medium. As shown in Table 7, formulations B and C showed greater stability that formulation A. The presence or absence of tissue culture medium in the formulations had a small, but measurable, effect on the stability of the rotavirus at 30° C. (compare B and C, Table 7). This effect was greater at 37° C. but still small compared to the standard (Formulation A). These data indicate that a wide concentration range (10–100%) of tissue culture medium is acceptable to attain improved stability.

TABLE 7

Potency loss (as log pfu/mL) of G1 rotavirus using formulations with and without tissue culture medium.

| | A | B | C |
|---|---|---|---|
| Loss after 1 week at 30° C. | 3.2 | 0.7 | 0.6 |
| Loss after 1 week at 37° C. | >6.5 | 0.6 | 1.0 |

To examine the effect of tissue culture medium at volume proportions of less than 10%, dialysis was employed to completely remove the tissue culture medium from the virus bulk. When a rotavirus liquid formulation was prepared from dialyzed virus bulk and thus contained 0% tissue culture media in the final formulation, these preparations inactivated faster than preparations in which rotavirus bulk was simply diluted into a stabilizer without tissue culture media (resulting in 10% tissue culture medium being present in the final vaccine formulation). This suggests that dialysis may have removed essential stabilizing components that are present in WE tissue culture medium. In the absence of an effective amount of tissue culture medium, divalent cations such as calcium can be added to the dialyzed vaccine formulation to improve stability (see Table 5). Dialysis at various processing scales can also be performed using diafiltration or ultrafiltration methods.

The stability of G1 reassortants was studied over a range of pH. Rotavirus G1 reassortant was formulated in 0.3 M sodium phosphate/0.1 M sodium citrate/50% sucrose stabilizer at different pH values. The viral titer indicates that under accelerated stability conditions, the stability of G1 reassortant is greater in the range from about pH 4.0 to about pH 8.0, particularly between about pH 5.0 to about pH 7.0. By "about pH" we mean within approximately 0.3 units of the stated pH value.

TABLE 8

Potency log loss of G1 rotavirus after 1 month at 30 or 37° C. in 0.3 M sodium phosphate/0.1 M sodium citrate/50% sucrose stabilizer at various pH values.

| | 1 month at 30° C. | 1 month at 37° C. |
|---|---|---|
| pH 3 | 4.6 | >6 |
| pH 4 | 1.3 | >6 |
| pH 5 | 1.3 | 1.5 |
| pH 6 | 1.3 | 1.4 |
| pH 7 | 1.4 | 2.2 |
| pH 8 | 1.6 | >6 |

b. Lyophilized Formulation Stability Data

Figure 8A:
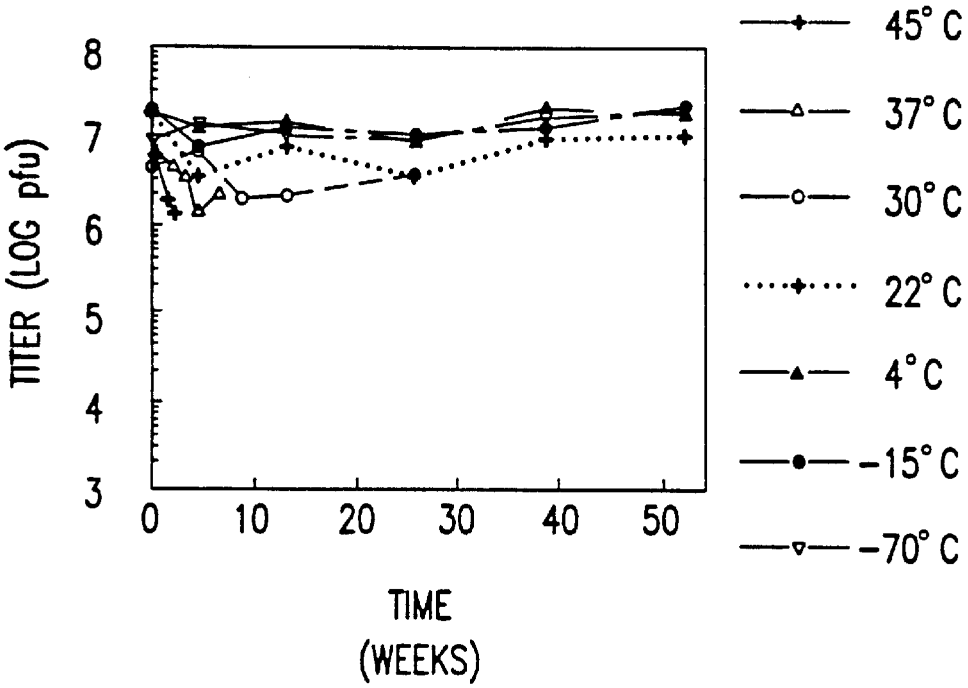
FIG. 8. Stability data for G1 rotavirus lyophilized formulations after storage at various temperatures. Panel A shows data for G1 rotavirus dialyzed prior to lyophilization into 1% sucrose, 4% mannitol, and 10 mM sodium phosphate. Stability data for vaccine dialyzed prior to lyophilization into 1% lactose, 4% mannitol, and 10 mM sodium phosphate is shown in panel B. Panel C shows data for G1 rotavirus diluted phosphate prior to lyophilization into 1% sucrose, 4% mannitol, and 75 mM sodium phosphate.
Figure 8B:
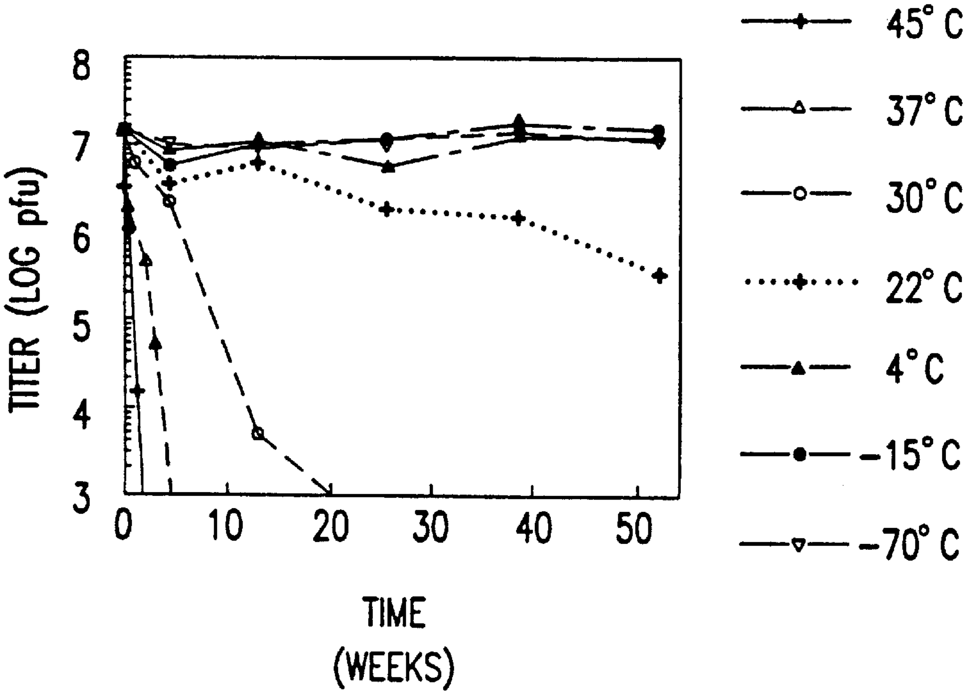
Figure 8C:
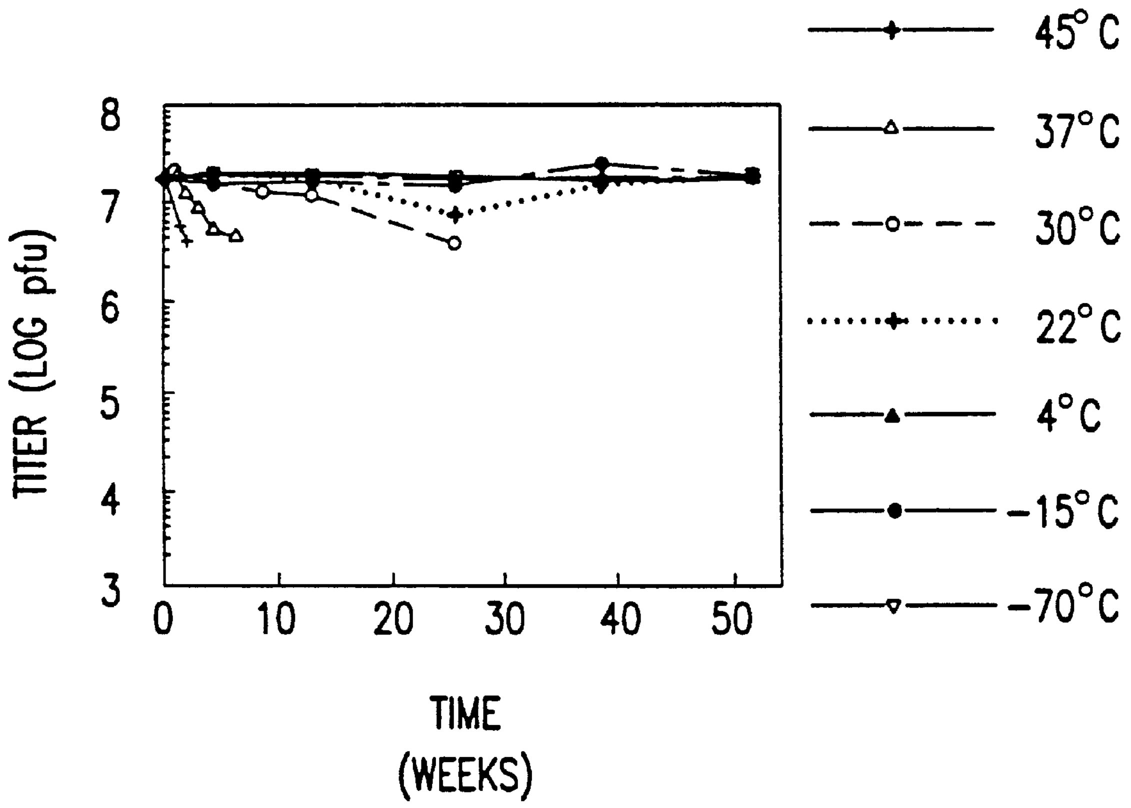
Figure 9A:
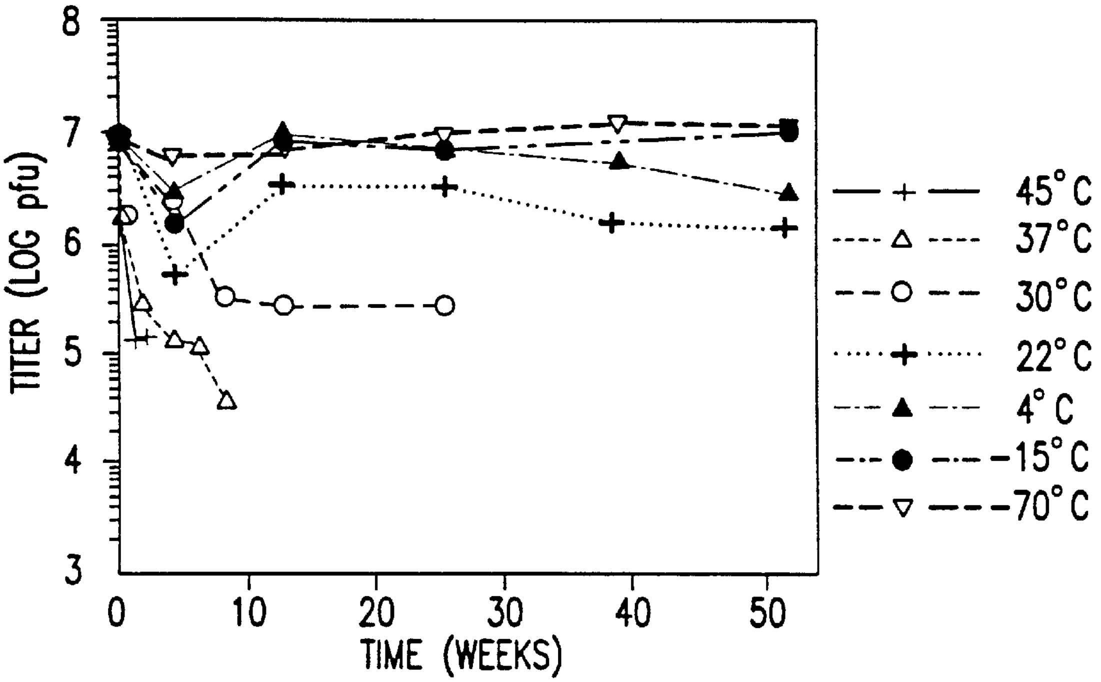
FIG. 9. Stability data for P1 rotavirus lyophilized formulations after storage at various temperatures. Panel A shows data for P1 rotavirus dialyzed prior to lyophilization into 1% sucrose, 4% mannitol, and 10 mM sodium phosphate. Stability data for vaccine dialyzed prior to lyophilization into 1% lactose, 4% mannitol, and 10 mM sodium phosphate is shown in panel B. Panel C shows data for P1 rotavirus diluted prior to lyophilization to 1% sucrose, 4% mannitol, and 75 mM sodium phosphate.
Figure 9B:
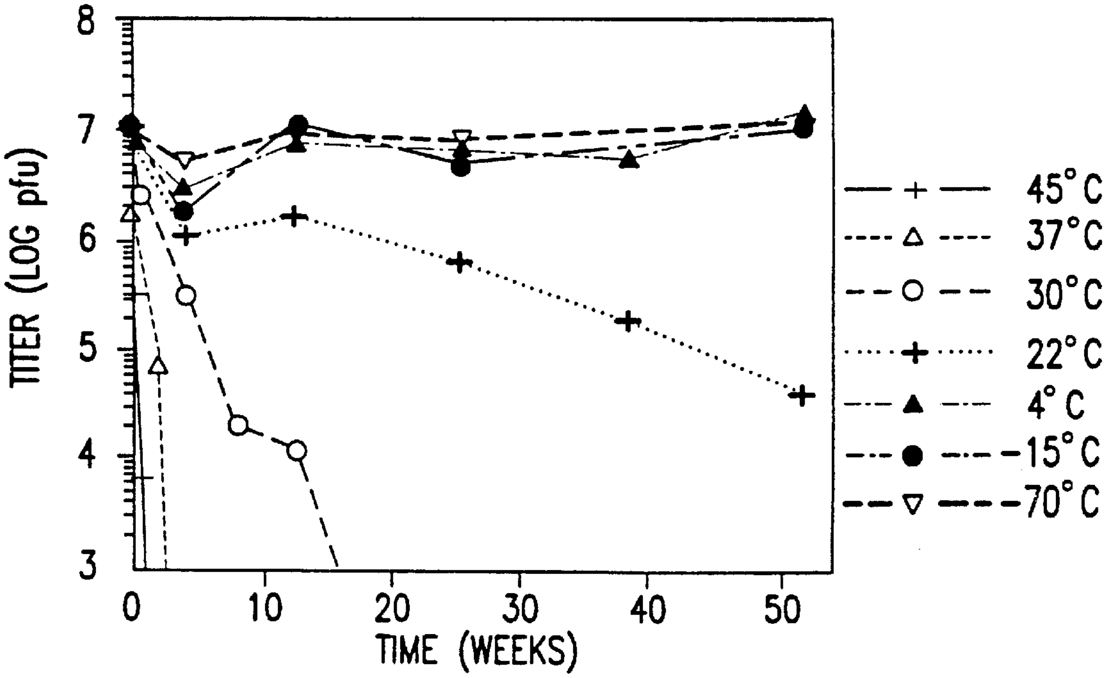
Figure 9C:
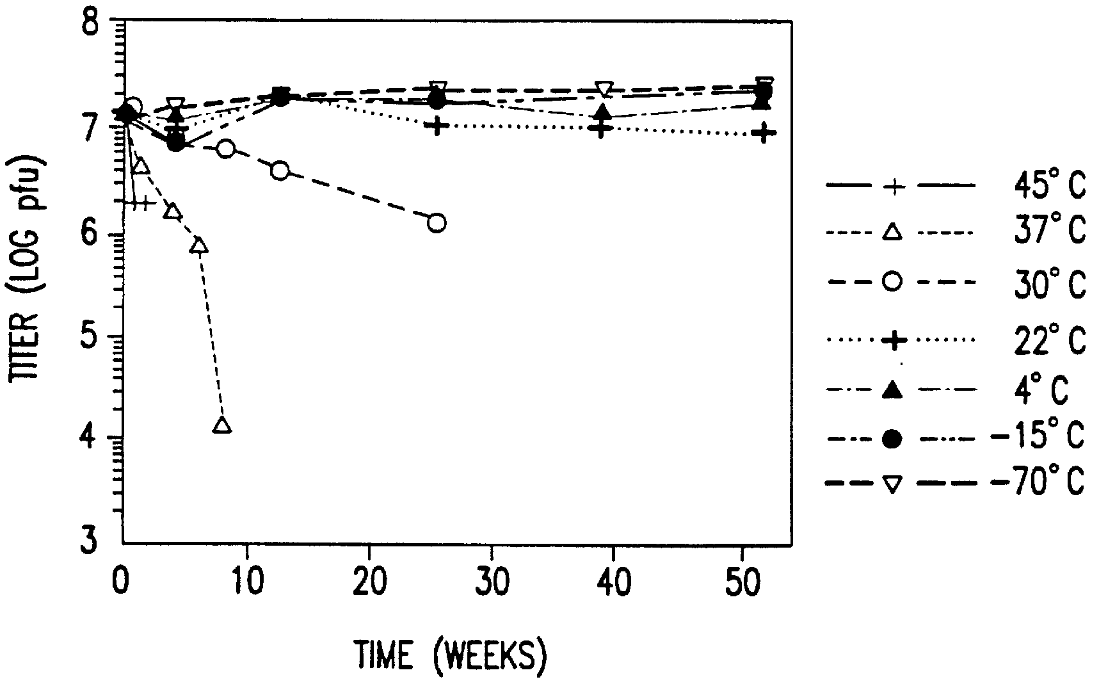
Figure 10:
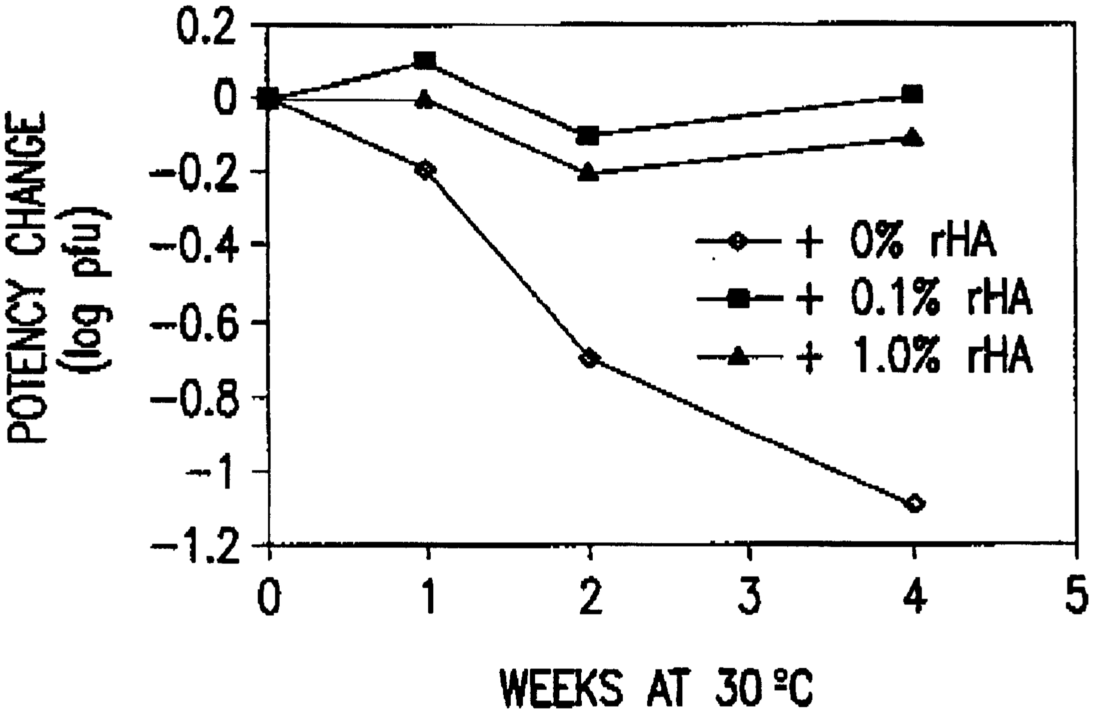
FIG. 10. Effect of recombinant human albumin (rHA) on the stability of G1 rotavirus in liquid formulation at 30° C. All values are expressed as loss in log pfu compared to −70° C. samples. The stabilizer is 50% sucrose 0.1 M phosphate/0.2 M citrate/WMEM/pH 6.2.

The G1 vaccine showed a 0.3 log loss after one year at 22° C. in a lyophilized formulation of 1% sucrose/4% mannitol/10 mM sodium phosphate at pH 7 (FIG. 8). Formulations containing 1% sucrose/4% mannitol/75 mM sodium phosphate at pH 7 showed no significant losses after one year at temperatures of 22° C. or below. P1 vaccines showed lower stability than the corresponding G1 formulations. In 1% sucrose/4% mannitol/10 mM sodium phosphate at 4° C. for one year, the P1 reassortant shows a 0.4 log loss in titer when compared with the vaccine stored at minus 70° C. (FIG. 9). A similar formulation with higher phosphate shows a loss in infectivity of less than 0.2 logs. The P1 vaccine in a phosphate, sucrose and hydrolyzed gelatin stabilizer shows no significant loss after one year at 4° C. These lyophilized formulations were prepared either by 10-fold dilution of rotavirus bulk into stabilizer (final concentration of 10% tissue culture medium) by dialysis of rotavirus bulk into stabilizer (complete removal of tissue culture medium).

EXAMPLE 4

An optimized formulation has been identified and is the lead candidate stabilizer for a rotavirus liquid vaccine. The final stabilizing formulation consists of 50% sucrose, 0.1 M phosphate, 0.2 M citrate, and WMEM at pH6.2. The base stabilizing formulation has an acid-neutralizing capacity (ANC) of 0.8 mEq/2 mL dose. The addition of polysorbate 80 or polysorbate 20 to this stabilizer further improved the stability of G1 reassortant rotavirus. As shown in the Table A, G1 rotavirus in the optimized formulation containing 0.01–0.1% polysorbate has improved stability from 4–30° C. compared to the optimized formulation without polysorbate.

Other non-ionic surfactants (besides the polysorbates, or Tween® surfactants, listed below) should be included in the patent. These include polysorbate 60 (Tween® 60), Brij 35®, Brij 58®, Triton X-100®, Triton X-114®, NP40®, Span 85, and the Pluronic® series of non-ionic surfactants (e.g., Pluronic 121).

TABLE A

Stability of G1 rotavirus at various temperatures in liquid formulations containing polysorbate. All values are expressed as loss in log pfu compared to −70° C. samples. The stabilizer is 50% sucrose/0.1 M phosphate/0.2 M citrate/WMEM/pH 6.2. Negative values indicate a higher potency compared to the control.

| Additional Excipient | Loss after 37° C. for 1 month | Loss after 30° C. for 1 month | Loss after 15° C. for 3 months | Loss after 4° C. for 3 months |
|---|---|---|---|---|
| none | 1.1 | 0.4 | 0.5 | 0.5 |
| 0.01% polysorbate 80 | 0.5 | 0.1 | 0.2 | −0.1 |
| 0.1% polysorbate 80 | 0.5 | 0.1 | 0.2 | −0.1 |
| 0.5% polysorbate 80 | 0.5 | 0.3 | 0.1 | −0.2 |
| 0.01% polysorbate 20 | 0.5 | 0.1 | 0.2 | −0.1 |
| 0.1% polysorbate 20 | 0.6 | 0.1 | 0.2 | −0.1 |
| 0.5% polysorbate 20 | 0.5 | 0.3 | 0.2 | −0.1 |

The stability of rotavirus can also be improved by the addition of recombinant human albumin (rHA). As shown below, the optimized formulation without rHA loses approximately one log of potency after four weeks at 30° C. in this experiment. The viral stability at this temperature is significantly improved by the addition of 0.1% (w/v) or 1.0% rHA to the stabilizer.

Lyophilized Formulations

Lead candidate formulations for a lyophilized rotavirus vaccine have been identified. These stabilizing formulations include 1% sucrose, 4% mannitol, 50% LPKM3 culture medium, and 10 mM sodium phosphate at pH 6.5. The stability of lyophilized rotavirus is further improved by the addition of up to 1% (w/v; 10 mg/mL) arginine to this stabilizer. The stabilities of G1 and G2 reassortant rotaviruses are further improved at temperatures ranging from 4–37° C. by the addition of arginine (Table B). Inclusion of arginine improves the stability of other rotavirus reassortants as well (Table C). As shown in Table D, other amino acids included in the sucrose/mannitol stabiliizer also improve the stability of rotavirus at 37° C.

A reconstitution buffer has been designed for lyophilized formulations. It provides additional acid-neutralizing capacity needed for buffering of gastric acid. This buffer consists of 50% sucrose and 0.7 M sodium citrate at pH 7 and has an ANC of 1.5 mEq/mL. No potency loss of rotavirus G1 was observed after reconstitution and incubation for 30 minutes at 37° C. or 2 hours at 30° C.

Lower concentrations of sucrose (range=0–50%) and citrate (range 0.2–0.7 M) also will have the desired effect. Even lower concentrations may be used if the reconstitution volume is increased.

TABLE B

Stability of rotavirus G1 and G2 in lyophilized formulations. All values are expressed as loss in log pfu/mL compared to −70° C. control. The stabilizer is 1% sucrose, 4% mannitol and 10 mM phosphate buffer at pH 6.5. All formulations contain 50% LPKM derived from viral bulks and diluents. Negative values indicate a higher potency compared to the control.

| Reassortant | Arginine | Loss after 3 months at 4° C. | Loss after 3 months at 15° C. |
|---|---|---|---|
| G1 | — | 0.4 | 0.2 |
| G1 | 1% | 0.1 | 0.0 |
| G2 | — | 0.2 | 0.1 |
| G2 | 1% | 0.0 | −0.2 |

TABLE C

Effect of arginine on the stability of five reassortants in lyophilized formulations. The values represent the loss in potency expressed as log pfu after incubation for one week at 37° C. The base stabilizer is 1% sucrose + 4% mannitol. Phosphate buffer at a concentration of 10 mM at pH 6.5 was used for all formulations. All formulations contain 50% LPKM culture medium derived from viral bulks and diluents. Negative values indicate a higher potency compared to the control.

| Reassortant | Stabilizer | Stabilizer + 1% Arginine |
|---|---|---|
| G1 | 0.7 | 0.2 |
| G2 | 0.4 | 0.0 |
| G3 | 0.7 | −0.1 |
| G4 | 0.2 | −0.1 |
| P1 | 0.0 | −0.1 |

TABLE D

Effect of amino acids on the stability of G1 and P1 rotaviruses in lyophilized formulation. The values represent the loss in potency expressed as log pfu after incubation for two weeks at 37° C. The base stabilizer is 1% sucrose + 4% mannitol. Phosphate buffer at a concentration of 10 mM at pH 6.5 was used for all formulations. All formulations contain 50% LPKM derived from viral bulks and diluents.

| Added amino acid | G1 | P1 |
|---|---|---|
| none | 1.6 | 2.1 |
| 1% glycine | 0.7 | 0.7 |
| 1% glutamine | 0.1 | 0.1 |
| 1% arginine | 0.6 | 0.0 |

What is claimed is:

1. A liquid rotavirus vaccine formulation comprising:

| | |
|---|---|
| a) at least one strain of rotavirus | about 1 × $10^5$ to about 1000 × $10^5$ pfu/mL; |
| b) Sugar | about 1 to about 70% (w/v); |
| c) Phosphate | about 0.01 to about 2 M; |
| d) at least one Carboxylate | about 0.05 to about 2 M; and |
| at least one component selected from the group consisting of | |
| e) about 0.5% to about 1.25% of recombinant human serum albumin and | |
| f) about 0.1% to about 2% polysorbate. | |

2. The formulation of claim 1 wherein said at least one carboxylate is selected from the group consisting of succinate, citrate, fumarate, tartarate, maleate and lactate.

3. The formulation according to claim 1 wherein said sugar is selected from the group consisting of sucrose, mannitol, lactose, sorbitol, dextrose, fucose, trehalose, polyaspartic acid, inositol hexaphosphate (phytic acid), sialic acid or N-acetylneuraminic acid-lactose.

4. The liquid vaccine formulation of claim 1 further comprising:

g) at least one diluent selected from the group consisting of Tissue culture medium, saline and water.

5. The formulation of claim 1 wherein the concentration of sugar is between about 5 to about 70%; the concentration of phosphate is between about 0.05 to about 0.3 M; and said at least one carboxylic acid is citrate or succinate at a concentration between about 0.05 to about 0.7M.

6. The formulation according to claim 1 wherein the pH is between about pH 5.0 to about pH 8.0.

7. The formulation according to claim 1 wherein said phosphate is selected from the group consisting of monophosphates, polyphosphates and phosphorylated compounds.

8. The formulation according to claim 7 wherein said phosphorylated compounds are phosphorylated sugars.

9. A method of preparing stabilized rotavirus vaccine formulations according to claim 1, comprising:

(a) cultivating a rotavirus and mixing the rotavirus with a concentrated stabilizing solution to form a virus bulk; and, optionally, (b) dialyzing the virus bulk or concentrated mixture to form a stabilized rotavirus vaccine solution according to claim 1.

10. A lyophilized rotavirus vaccine formulation comprising:

| | |
|---|---|
| a) at least one strain of rotavirus | about 1 × $10^5$ to about 1000 × $10^5$ pfu/mL; |
| b) at least one sugar | about 1 to about 20% (w/v); |
| c) Phosphate | about 0.05 to about 2 M; and |
| at least one component selected from the group consisting of | |
| d) about 0.5% to about 1.25% of recombinant human serum albumin and | |
| e) about 0.1% to about 1.25% of at least one amino acid selected from the group consisting of glutamate, glutamine and arginine. | |

11. The formulation according to claim 10 wherein said at least one sugar is selected from the group consisting of Sucrose, Mannitol and Lactose.

12. The formulation of claim 10 wherein:

| | |
|---|---|
| a) said at least one sugar is selected from the group consisting of Sucrose and lactose | about 1% (w/v); |
| b) said formulation further comprises Mannitol | about 4% (w/v); and |
| c) said Phosphate | about 0.010 to about 0.075 M. |

13. The formulation according to claim 10 wherein after reconstitution, the pH is between about pH 5.0 to about pH 7.0.

* * * * *